US010179930B2

(12) United States Patent
Celedon et al.

(10) Patent No.: US 10,179,930 B2
(45) Date of Patent: Jan. 15, 2019

(54) DETECTION UNITS AND METHODS FOR DETECTING A TARGET ANALYTE

(71) Applicant: Scanogen Inc., Baltimore, MD (US)

(72) Inventors: Alfredo Andres Celedon, Columbia, MD (US); Saravana Radha Krishna Murthy, Gaithersburg, MD (US); Zhiguang Xu, Baltimore, MD (US); Danielle Elise Schultz, Gaithersburg, MD (US); Troy Allen Horn, Reisterstown, MD (US)

(73) Assignee: Scanogen Inc., Baltimore, MD (US)

( * ) Notice: Subject to any disclaimer, the term of this patent is extended or adjusted under 35 U.S.C. 154(b) by 328 days.

(21) Appl. No.: 15/033,629

(22) PCT Filed: Feb. 5, 2015

(86) PCT No.: PCT/US2015/014616
§ 371 (c)(1),
(2) Date: Apr. 30, 2016

(87) PCT Pub. No.: WO2015/120147
PCT Pub. Date: Aug. 13, 2015

(65) Prior Publication Data
US 2016/0258003 A1     Sep. 8, 2016

Related U.S. Application Data

(60) Provisional application No. 61/936,863, filed on Feb. 6, 2014.

(51) Int. Cl.
| | |
|---|---|
| *C12Q 1/68* | (2018.01) |
| *G01N 33/53* | (2006.01) |
| *C12Q 1/6816* | (2018.01) |
| *G01N 33/543* | (2006.01) |

(52) U.S. Cl.
CPC ..... *C12Q 1/6816* (2013.01); *G01N 33/54306* (2013.01); *G01N 33/54313* (2013.01); *G01N 33/54373* (2013.01)

(58) Field of Classification Search
None
See application file for complete search history.

(56) References Cited

U.S. PATENT DOCUMENTS

| 7,736,889 B2 | 6/2010 | Rife |
| 9,382,578 B2 | 7/2016 | Celedon |
| 9,382,580 B2 | 7/2016 | Celedon |
| 2002/0115088 A1 | 8/2002 | Kurn |
| 2003/0207296 A1 | 11/2003 | Park |
| 2004/0234970 A1 | 11/2004 | Yoo |
| 2010/0234234 A1 | 9/2010 | Ferrigno |
| 2010/0253328 A1 | 10/2010 | Celedon |
| 2010/0267169 A1 | 10/2010 | Hajimiri |
| 2011/0015380 A1 | 1/2011 | Vezenov |
| 2012/0115744 A1 | 5/2012 | Raymond |

FOREIGN PATENT DOCUMENTS

| WO | WO 9936577 A1 | 7/1999 |
| WO | WO 0061803 A1 | 10/2000 |
| WO | WO 02/059364 A1 | 8/2002 |
| WO | WO 2010021639 A1 | 2/2010 |
| WO | WO 2011045570 A2 | 4/2011 |
| WO | WO 2011087916 A2 | 7/2011 |
| WO | WO 2012071428 A2 | 5/2012 |
| WO | WO 2013059044 A1 | 4/2013 |
| WO | WO 2015195404 A1 | 12/2015 |

OTHER PUBLICATIONS

Justin, Gusphyl A., et al., "Hydrodynamic focusing for impedance-based detection of specifically bound microparticles and cells: Implications of fluid dynamics on tunable sensitivity." Mar. 15, 2012, Sensors and Actuators B: Chemical 166-167 (2012) 386-393, Elsevier B.V.
Supplementary European Search Report dated May 11, 2017 in European Application No. EP 17 74 6242.
Silver, J., et al., "Tethered-bead, immune sandwich assay." Biosensors and Bioelectronics, 63, pp. 117-123, Jul. 11, 2014.
Mulvaney, S.P., et al., "Rapid, femtomolar bioassays in complex matrices combining microfluidics and magnetoelectronics." Biosensors and Bioelectronics 23 (2007) 191-200.
Han, KC, et al., "Elongated oligonucleotide-linked immunosorbent assay for sensitive detection of a biomarker in a microwell plate-based platform." Dec. 15, 2013, Biosens Bioelectron 50:421-4, Elsevier B.V.
Yang, CJ, et al., "Linear molecular beacons for highly sensitive bioanalysis based on cyclic Exo III enzymatic amplification." Sep. 15, 2011, Biosens Bioelectron 27(1):119-24, Elsevier B.V.
Revyakin, A, et al., "Single-molecule DNA nanomanipulation: Improved resolution through use of shorter DNA fragments." Feb. 2005, Nature Methods, vol. 2 No. 2 pp. 127-138, Cold Spring Harbor Laboratory Press.
Smith, SB, et al., "Direct Mechanical Measurements of the Elasticity of Single DNA Molecules by Using Magnetic Beads." Science, New Series, vol. 258, No. 5085 (Nov. 13, 1992), 1122-1126, American Association for the Advancement of Science.
Celedon, A, et al., "Torsional Mechanics of DNA are Regulated by Small-Molecule Intercalation." J.Phys.Chem. B, Nov. 24, 2010, vol. 114, No. 50, pp. 16929-16935.
International Search Report and Written Opinion from PCT/US2012/059497 dated Dec. 26, 2012, 11 pages.
Lipfert, J, et al., "Torsional sensing of small-molecule binding using magnetic tweezers." Nucleic Acids Research, 2010, vol. 38, No. 20, 7122-7132.

(Continued)

*Primary Examiner* — James Martinell
(74) *Attorney, Agent, or Firm* — Shores & Oliver, P.C.; Glenn E. Karta

(57) ABSTRACT

The present application relates to detection units and methods for detecting one or more target analytes in a sample using a complex formed by a target and first and second probes, wherein the complex comprises an elongated region, a particle that is coupled to the first probe, and a solid support that is coupled to the second probe. Specific binding of a target analyte can be distinguished from non-specific binding of the particle by measuring the displacement of the particle.

36 Claims, 8 Drawing Sheets

(56) References Cited

OTHER PUBLICATIONS

Carrasco Pulido, C., et al., "Magnetic Tweezers." In: Encyclopedia of Life Sciences (ELS). John Wiley & Sons, Ltd: Chichester. Apr. 2011.

Lipfert, J, et al., "Quantitative Modeling and Optimization of Magnetic Tweezers." Biophysical Journal, vol. 96, Jun. 2009, 5040-5049.

Celedon, A., et al., "Magnetic Tweezers Measurement of Single Molecule Torque." Nano Letters, Mar. 20, 2009, vol. 9, No. 4, 1720-1725.

Mulvaney, et al.: "Direct detection of genomic DNA with fluidic force discrimination assays" Anal. Biochem., vol. 392, No. 2, 2009, pp. 139-144, Elsevier.

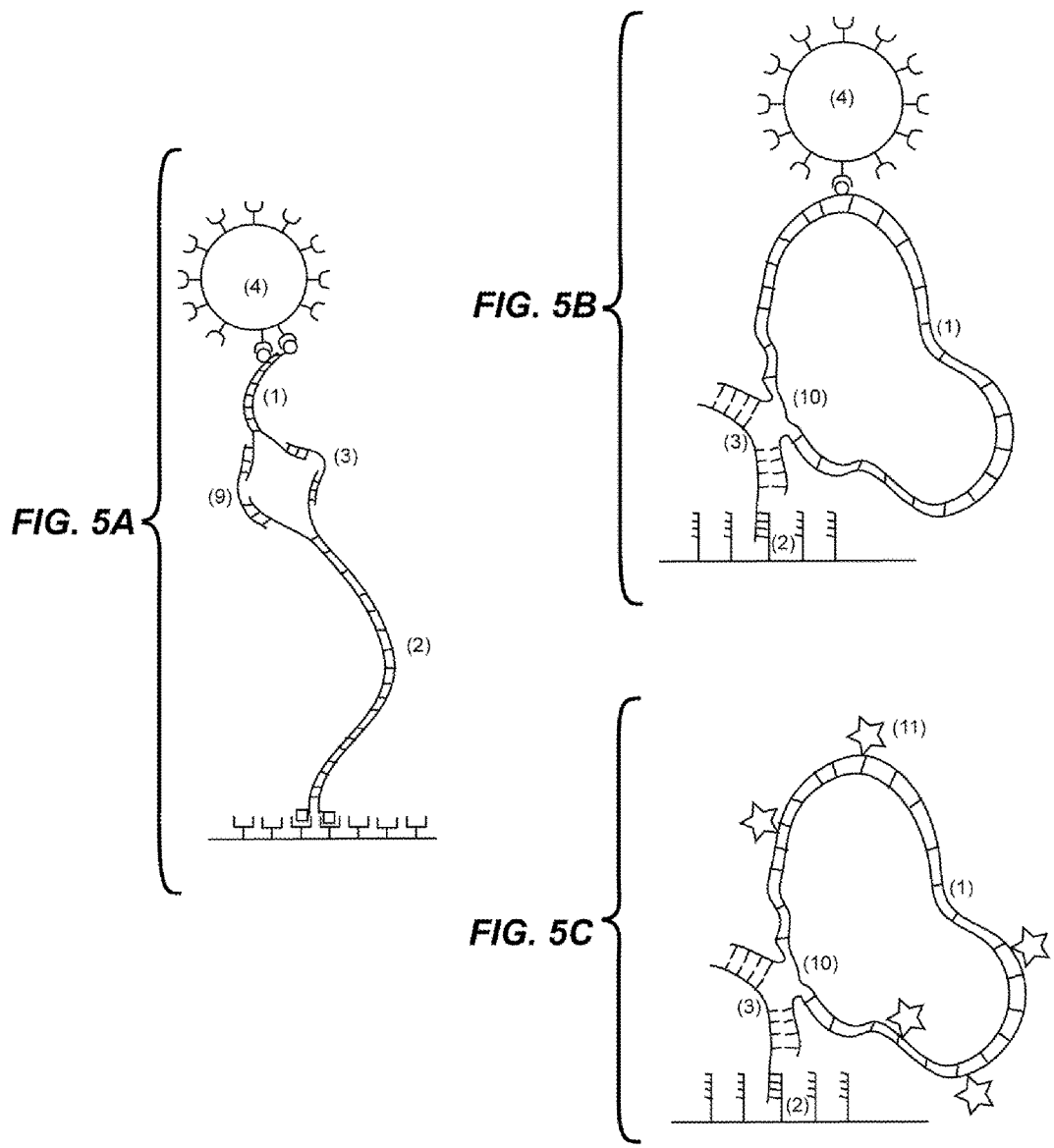

DETECTION UNITS AND METHODS FOR DETECTING A TARGET ANALYTE

CROSS REFERENCE TO RELATED APPLICATIONS

The present application claims the benefit of U.S. Provisional Application No. 61/936,863 filed Feb. 6, 2014, the contents of which are incorporated by reference herein in their entirety.

STATEMENT REGARDING FEDERALLY SPONSORED RESEARCH OR DEVELOPMENT

This invention was made with government support under Federal Award Identification Number R21CA174594 awarded by the Department of Health and Human Services/National Institutes of Health/National Cancer Institute. The government has certain rights in the invention.

FIELD OF THE INVENTION

The present invention relates generally to detection units and methods for detecting a target analyte such as natural, synthetic, modified or unmodified nucleic acids or proteins in a sample.

BACKGROUND OF THE INVENTION

Many detection systems for determining the presence or absence of a particular target analyte in a sample are known. Examples of detection systems for detecting analytes include immunoassays, such as an enzyme linked immunosorbent assays (ELISAs), which are used in numerous diagnostic, research and screening applications. Generally, these detection systems detect the target analyte when it binds to a specific binding agent or probe resulting in a measurable signal.

When using known detection systems, such as immunoassays, the ability to detect a target analyte is often limited by the low concentration of the target analyte in the sample and by non-specific interactions, such as non-specific binding of signal producing molecules and non-specific binding of sample molecules. The ability to detect a target analyte in a biological sample is often limited by these two factors.

The signal generated by detection systems is normally proportional to the number of target analytes that bind to the specific binding probe. Therefore, when the concentration of target is low, the signal is low. The total signal can be increased by increasing the signal associated with each bound target analyte. Often, detection systems use a solid support and reporter markers, such as fluorescent molecules, to generate the signal. Several strategies that use reporter markers have been designed to increase the signal associated with each bound target, such as in branched-DNA (Hendricks et al., Am J Clin Pathol. 1995, 104(5):537) and hybrid capture (WO 2003078966 A2). While these strategies increase the total signal, they often also increase the background noise resulting from the non-specific interaction between the reporter marker and the solid support. These strategies do not offer an effective method of discriminating reporter markers non-specifically bound to the solid support.

The use of micrometer scale particles as reporter markers, described in PCT/GB2010/001913, offers a method to remove particles non-specifically bound to the solid support by applying a controlled fluid drag force on the particles. However, the drag force significantly reduces the signal as well as the background noise because the disrupting force experienced by the target containing tethers is as high as the force experienced by the non-specific tethers.

Another strategy, disclosed in PCT/GB2010/001913 (WO 2011/045570 A2), uses a magnetic bead tethered to a solid support by an elongated molecule as a sensing apparatus to detect, for example a signal from an ELISA assay. According to this disclosure, the bead is tethered to the solid support independently of the presence or absence of target molecules and the signal is amplified be releasing manipulating agents that act on the elongated molecule. This strategy does not provide a simple method to discriminate non-specific interactions.

Accordingly, there is a need for a detection unit and systems of such units as well as methods capable of detecting low concentrations of target analytes while distinguishing non-specific binding from specific binding in the sample.

SUMMARY OF THE INVENTION

In one aspect, the present invention provides a method of detecting a target analyte in a sample comprising:
a) providing a complex formed from:
  i) a first probe coupled to a particle and bound to said analyte if present, and
  ii) a second probe coupled to a solid support and bound to said analyte if present, so that if the target analyte is present in the sample, the particle is indirectly coupled to the solid support via a complex formed by the target analyte and the first and second probes, and wherein the complex comprises an elongated region; and
b) either i) applying a force to the indirectly coupled particle or to the complex comprising the elongated region and measuring the amount of particle displacement or the length of the complex, wherein the amount of displacement or length of the complex indicates whether or not the target analyte is present in the sample, or ii) measuring the Brownian motion of the indirectly coupled particle, wherein the amount of Brownian motion indicates whether or not the target analyte is present in the sample.

In another aspect, the present invention provides a kit for detecting a target analyte in a sample, the kit comprising a) a particle; and b) a first probe capable of binding to said analyte, and to either a solid support or to said particle, said first probe optionally comprising an elongated region between about 0.15 and about 20 µm long; c) packaging material; and optionally d) instructions for use.

In yet another aspect, the present invention provides a method of detecting a target analyte in a sample, the method comprising:
a) providing a complex formed from:
  i) a first probe coupled to a particle and bound to said analyte if present, and
  ii) a second probe coupled to a substantially flat solid support and bound to said analyte if present,
so that if the target analyte is present in the sample, the particle is indirectly coupled to the solid support via a complex formed by the target analyte and the first and second probes, and wherein the complex comprises an elongated region; and
b) applying a force to the indirectly coupled particle using a flow substantially parallel to the solid support that removes non-specifically bound particles, wherein the presence of the particle after the application of force indicates the presence of the target analyte in the sample.

While certain particles (e.g., micrometer scale magnetic beads) can be used to increase the sensitivity of detection systems to generate a measurable signal, these particles are prone to non-specific interactions with the solid support to which the probe is attached, creating background noise. However, by using a particle indirectly coupled to the solid support via a complex formed by the target analyte and the first and second probes, and wherein the complex comprises an elongated region, specific binding to a target analyte can be distinguished from non-specific binding by measuring the displacement of the particle. Particles that are coupled to the solid support via the complex are displaced by a distance that is a function of the length of the elongated region. Particles that are non-specifically bound to the solid support are displaced by a distance less than the particles that are specifically coupled to the solid support via the complex. In this way, displacement of the particles can be used to distinguish specific from non-specific binding, particularly in samples with low concentrations of target analyte. Other non-specific interactions that can produce the non-specific attachment of a particle to the solid support can also be distinguished, such as particles that non-specifically bind to a probe, or probes that non-specifically bind to the solid support, because those particles are also displaced by a distance less than the particles that are specifically coupled to the solid support via a complex.

Using a particle indirectly coupled to the solid support via a complex formed by the target analyte and the first and second probes, and wherein the complex comprises an elongated region in embodiments of this invention has at least three additional advantages over other systems that use reporter markers. First, using a complex with an elongated region creates a simple multiplexing method. Detection of multiple targets in a single assay is possible by using elongated regions of different size for each different target. Particle displacement and therefore elongated region length can be easily measured in thousands of complexes with sub-micrometer resolution as demonstrated in Example 3. Second, in some embodiments, the application of force can increase the target selectivity of the technique by removing particles that are bound via molecules in the sample that are similar to but not exactly the same as the target molecule. Third, in embodiments that apply a force substantially parallel to the solid support, such as embodiments that apply fluid drag substantially parallel to the solid support, force can remove non-specifically bound particles while not significantly reducing the signal because being part of a complex with an elongated region reduces the force experienced by the target analyte. When force substantially parallel to the solid support is applied on particles bound to the solid support, the tension on the tether decreases with tether length (Langmuir (1996) 12(9): 2271). Therefore, non-specific interactions, which are normally tethers about 10 nm long, experience tensions that are significantly higher than the tension that a target bound in an elongated complex experience. This property of long tethers allows in embodiments of the present invention the removal of non-specifically bound particles without significantly affecting specifically bound particles.

In another embodiment, the method comprises: a) providing a probe and a particle, wherein the probe comprises a first end for coupling to a solid support, a second end comprising a first analyte binding region, and an elongated region disposed between the first and second end, and wherein the particle comprises a second analyte binding region; b) exposing the probe to the sample, wherein if the target analyte is present in the sample, the target analyte binds to the first analyte binding region of the probe; c) exposing the particle to the sample, wherein if the target analyte is present in the sample, the target analyte binds to the second analyte binding region of the particle; d) exposing the probe to the solid support, under conditions that permit the coupling of the first end of the probe to the solid support, so that if the target analyte is present in the sample, the particle is indirectly coupled to the solid support via the target analyte and the probe; e) applying a force to the particle; and f) measuring the amount of particle displacement, wherein the amount of displacement indicates whether or not the target analyte is present in the sample.

In another embodiment, the method for detecting a target analyte in a sample comprises: a) providing a probe and a solid support, wherein the probe comprises a first end for coupling to a particle, a second end comprising a first analyte binding region, and an elongated region disposed between the first and second ends, and wherein the solid support comprises a second analyte binding region; b) exposing the probe to the sample, wherein if the target analyte is present in the sample, the target analyte binds to the first analyte binding region of the probe; c) exposing the probe to the particle, under conditions that permit the coupling of the first end of the probe to the particle d) exposing the solid support to the sample, wherein if the target analyte is present in the sample, the target analyte binds to the second analyte binding region of the solid support, so that the particle is indirectly coupled to the solid support via the target analyte and the probe; e) applying a force to the particle; and f) measuring the amount of particle displacement, wherein the amount of displacement indicates whether or not the target analyte is present in the sample.

In certain embodiments, the first analyte binding molecule of the probe comprises a first nucleic acid that hybridizes to a first region of the target analyte and the second analyte binding region comprises a second nucleic acid that hybridizes to a second region of the target analyte. In certain other embodiments, the first analyte binding region of the probe comprises a first antibody that binds to the target analyte and the second analyte binding region comprises a second antibody that binds to the target analyte.

In yet another embodiment, the method for detecting a target analyte in a sample comprises: a) providing 1) a first probe comprising a first end for coupling to a particle and a second end comprising a first analyte binding region and 2) a second probe comprising a first end for coupling to a solid support and a second end comprising a second analyte binding region, wherein at least one of the first or second probes comprise an elongated region disposed between the first and the second end; b) exposing the first probe and the second probe to the sample, wherein if the target analyte is present in the sample, a first region of the target analyte binds to the first analyte binding region of the first probe and a second region of the target analyte binds to the second analyte binding region of the second probe; c) exposing the first probe to a particle under conditions that permit the coupling of the first end of the first probe to the particle; d) exposing the second probe to the solid support under conditions that permit the coupling of the first end of the second probe to the solid support, so that if the target analyte is present in the sample, the particle is indirectly coupled to the solid support via the first probe, which is bound to the target analyte, which is bound to the second probe, which is coupled to the solid support; e) applying a force to the particle; and f) measuring the amount of particle displacement, wherein the amount of displacement indicates whether or not the target analyte is present in the sample.

In yet other embodiments, the first probe and second probes bind to locations in the target analyte that are separated by an elongated region in the target analyte. In these embodiments the elongated region in the complex may coincide in part or totally with the elongated region of the target analyte.

In certain embodiments, the first analyte binding region of the first probe comprises a first nucleic acid that hybridizes to a first region of the target analyte and the second analyte binding region of the second probe comprises a second nucleic acid that hybridizes to a second region of the target analyte. In other embodiments, the first analyte binding region of the first probe comprises a first antibody that binds to the target analyte and the second analyte binding region of the second probe comprises a second antibody that binds to the target analyte.

In certain embodiments, the first probe comprises an elongated nucleic acid disposed between its first and second end, while in other embodiments, the second probe comprises an elongated nucleic acid disposed between its first and second end. In yet other embodiments, the first probe comprises a first elongated nucleic acid disposed between its first and second end and the second probe comprises a second elongated nucleic acid disposed between its first and second end.

In the methods described herein, the exposing steps (b), (c), and (d), can be performed in any order, or simultaneously. Thus, in certain embodiments, the order of the steps b), c) and d) is b-d-c; c-b-d; c-d-b; d-b-c; or d-c-b. In other embodiments, two out of the three steps b), c) and d) are conducted simultaneously. In certain embodiments, the exposure of the sample to the first probe is conducted before, after, or simultaneously with the exposure of the sample to the second probe. In other embodiments, steps b), c) and d) are conducted simultaneously.

In certain embodiments, the methods comprise a washing step after step b) and/or step c) and/or step d).

In certain embodiments, the force applied to the particle is a magnetic force, fluid drag, fluid buoyancy, mechanical force, electrical force, centrifugal force, gravitational force, or a combination thereof.

In certain embodiments, the elongated region ranges from about 0.15 µm to about 20 µm in length. In other embodiments, the elongated nucleic acid ranges from about 0.5 µm to about 5 µm in length.

In certain embodiments, the diameter of the particle ranges from about 0.3 µm to about 20 µm. In certain other embodiments, the particle is a magnetic particle, including, but not limited to a superparamagnetic particle.

In certain embodiments, instead of measuring the displacement of the particle generated by the force with or without application of force in step f), the Brownian motion of the particle is measured, wherein the amount of Brownian motion indicates whether or not the target analyte is present in the sample.

In certain embodiments, the displacement of the particle is measured using an imaging system with a lens, or with a lens-free microscope or with a coherent imaging technique.

In certain embodiments, the target analyte is a nucleic acid molecule selected from, single stranded DNA or single stranded RNA such as, messenger RNA, small interfering RNA, micro-RNA and its precursors or circulating RNA. In certain embodiments, the temperature of the sample is controlled to produce denaturation of double stranded nucleic acids in the sample and/or specific hybridization of nucleic acids in the sample to the first and second analyte binding region. In other embodiments, the sample is initially treated with an exonuclease enzyme to convert double stranded nucleic acids into single stranded nucleic acids. In other embodiments, the target analyte is a protein.

Another aspect of the invention relates to a kit or detection unit for identifying a target analyte in a sample. The kit or detection unit comprises a first probe comprising a first end for coupling to a surface or a particle, a second end comprising an analyte binding region, and an elongated region disposed between the first and second end. According to this embodiment, the first probe binds to the target analyte. The first probe also allows the amount of displacement of a particle bound thereto to be distinguished from the amount of displacement of a particle bound non-specifically to a solid support to which the probe is bound. In one embodiment, the elongated region is a nucleic acid between 0.5 and 10 µm long. In another embodiment, the kit or detection unit further comprises a second probe comprising a first end for coupling to a solid support or a particle and a second end comprising a second analyte binding region, wherein if the first end of the first probe is for coupling to a solid support, the first end of the second probe is for coupling to the particle and if the first end of the first probe is for coupling to the particle, the first end of the second probe is for coupling to the solid support.

BRIEF DESCRIPTION OF THE FIGURES

FIG. 5A depicts an embodiment wherein the first (1) and second (2) probes are capable of binding both the target analyte (3) and a second molecule (9), and a rotational force is applied to the complex which may result in detectable coiling or supercoiling of the complex.

FIG. 5B depicts an embodiment wherein the first probe comprises an elongated circular double stranded DNA (1). The circular double stranded DNA has a region which is single stranded where one of the strands is discontinuous (10). Target (3) binding to the first probe (1) bridges the discontinuous strand, and a rotational force is applied to the complex which may result in detectable coiling or supercoiling of the complex. The second probe (2) binds to the target and couples to the solid support.

FIG. 5C depicts an embodiment wherein the first probe comprises an elongated circular double stranded DNA (1) having one or more fluorescent labels (11). The circular double stranded DNA has a region which is single stranded where one of the strands is discontinuous (10). Target (3) binding to the first probe (1) bridges the discontinuous strand, and a rotational force is applied to the complex which may result in detectable supercoiling of the complex. The second probe (2) binds to the target and couples to the solid support.

DETAILED DESCRIPTION OF THE INVENTION

Figure 1A:
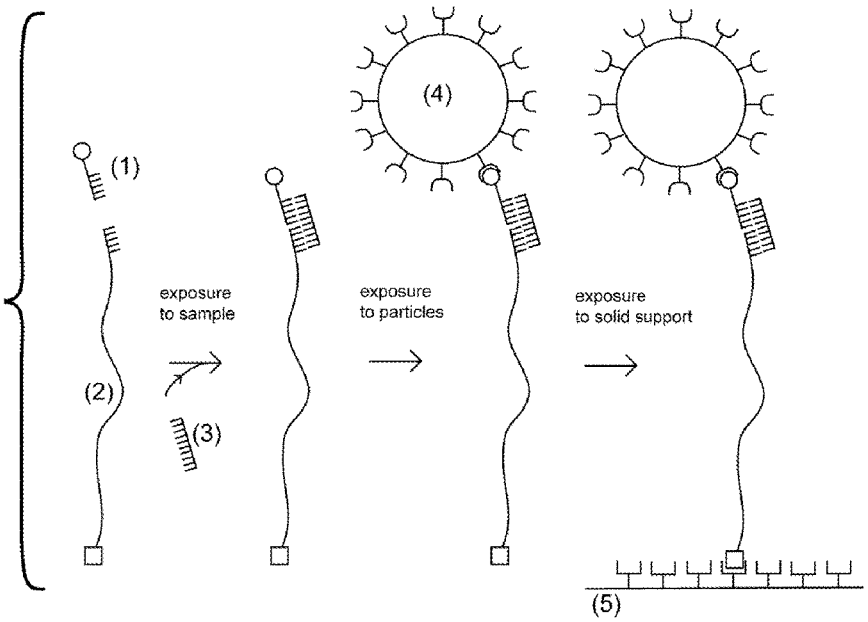
FIG. 1A depicts an embodiment wherein the first probe (1) and second probe comprising an elongated region (2) are exposed to a sample under conditions such that if the target analyte (3) is present in the sample then it binds to the first probe (1) and the second probe (2). Upon exposure of a particle (4) to the sample, the particle (4) couples to the first probe (1). Upon exposure to a solid support (5), the second probe (2) couples to the solid support (5).

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The terms "about" and "substantially" are used herein to mean approximately, in the region of, roughly, or around. When the terms "about" and "substantially" are used in conjunction with a numerical range, it modifies that range by extending the boundaries above and below the numerical values set forth. In general, the terms "about" and "substantially" are used herein to modify a numerical value above and below the stated value by a variance of less than about 20%.

Technical and scientific terms used herein have the meaning commonly understood by one of skill in the art to which the present application pertains, unless otherwise defined. Reference is made herein to various methodologies and materials known to those of skill in the art. Standard reference works setting forth the general principles of recombinant DNA technology include Sambrook et al., "Molecular Cloning: A Laboratory Manual," 2nd Ed., Cold Spring Harbor Laboratory Press, New York (1989); Kaufman et al., Eds., "Handbook of Molecular and Cellular Methods in Biology in Medicine," CRC Press, Boca Raton (1995); and McPherson, Ed., "Directed Mutagenesis: A Practical Approach," IRL Press, Oxford (1991), the disclosures of each of which are incorporated by reference herein in their entireties.

The terms "target analyte" or "analyte," are used herein to denote the molecule to be detected in the test sample. According to the invention, there can be any number of different target analytes in the test sample (from one to one thousand, or even more). The target analyte can be any molecule for which there exists a naturally or artificially prepared specific binding member. Examples of target analytes include, but are not limited to, a nucleic acid, oligonucleotide, DNA, RNA, protein, peptide, polypeptide, amino acid, antibody, carbohydrate, lipid, hormone, steroid, toxin, vitamin, any drug administered for therapeutic and illicit purposes, a bacterium, a virus, cell, as well as any antigenic substances, haptens, antibodies, metabolites, water pollutants (such as nitrates, phosphates, heavy metals, etc.) and molecules having an odor, such as compounds containing sulfur and/or nitrogen, for example hydrogen sulfide, ammonia, amines, etc., and combinations thereof.

In a preferred embodiment, the target analyte is a nucleic acid. The nucleic acid can be from any source in purified or unpurified form including DNA (dsDNA and ssDNA) and RNA, including tRNA, mRNA, rRNA, siRNA, mitochondrial DNA and RNA, chloroplast DNA and RNA, DNA-RNA hybrids, or mixtures thereof, genes, chromosomes, plasmids, the genomes of biological materials, including microorganisms such as bacteria, yeast, viruses, viroids, molds, fungi, plants, animals, humans, and fragments thereof. The nucleic acid can be single stranded DNA obtained by exposing double stranded DNA to an exonuclease enzyme, such as exonuclease III. The target analyte can be obtained from various biological materials by procedures well known in the art.

In another preferred embodiment, the target analyte is a short nucleic acid containing less than about 200 base pairs or less than about 200 nucleotides. In general, such molecules are difficult to detect using PCR-based techniques because suitable primers often cannot be found in such a short sequence. A particular case of small DNA molecules are molecules of less than about 40 nucleotides. These molecules are smaller than the combined size of standard PCR primers (each primer about 20 nucleotides). Short nucleic acid molecules are common in nature, exemplary cases are small interfering RNA (siRNA), micro-RNA (miRNA) and its precursors, pri-miRNA and pre-miRNA, and fragmented DNA molecules produced after cell death and present in blood, urine and other body fluids.

The term "probe" is understood herein to mean one or more molecules that are capable of binding to the target analyte and also being coupled to, depending on the context, either a solid support or a particle. Probes have a region capable of binding to the target analyte. The term "first probe" is understood herein to mean the probe that is capable of coupling to a particle. The term "second probe" is understood herein to mean the probe that is capable of coupling to the solid support. For example, if the target analyte is a nucleic acid, oligonucleotide, DNA, or RNA, the region capable of binding the target analyte in both the first and second probe may comprise a nucleic acid, oligonucleotide, DNA, or RNA molecule having a sequence complementary to the target analyte and capable of hybridizing thereto. As another example, if the target analyte is a protein, peptide, polypeptide, or amino acid, the region capable of binding the target analyte in both the first and second probe may comprise an antibody or an antigen-binding fragment that specifically binds to the target analyte.

The terms "coupling", "to couple" and "coupled" refer to a covalent or non-covalent bond between a probe and a surface, or between a probe and another molecule covalently or non-covalently linked to the surface. The terms "binding," "binds," or "bound" refer to a covalent or non-covalent interaction between a probe and a target analyte. In either case, non-covalent interactions could be, for example, ionic, via hydrogen bonding, etc.

The term "antibody" as used in this disclosure refers to an immunoglobulin or an antigen-binding fragment thereof.

The term "antigen-binding fragment" refers to a part of an antibody molecule that comprises amino acids responsible for the specific binding between antibody and antigen. For certain antigens, the antigen-binding domain or antigen-binding fragment may only bind to a part of the antigen. The part of the antigen that is specifically recognized and bound by the antibody is referred to as the "epitope" or "antigenic determinant." Antigen-binding domains and antigen-binding fragments include Fab (Fragment antigen-binding); a F(ab')$_2$ fragment, a bivalent fragment having two Fab fragments linked by a disulfide bridge at the hinge region; Fv fragment; a single chain Fv fragment (scFv) see e.g., Bird et al. (1988) *Science* 242:423-426; and Huston et al. (1988) *Proc. Natl. Acad. Sci. USA* 85:5879-5883); a Fd fragment having the two $V_H$ and $C_H1$ domains; dAb (Ward et al., (1989) *Nature* 341:544-546), and other antibody fragments that retain antigen-binding function. The Fab fragment has $V_H$-$C_H1$ and $V_L$-$C_L$ domains covalently linked by a disulfide bond between the constant regions. The $F_v$ fragment is smaller and has $V_H$ and $V_L$ domains non-covalently linked. To overcome the tendency of non-covalently linked domains to dissociate, a $scF_v$ can be constructed. The $scF_v$ contains a flexible polypeptide that links (1) the C-terminus of $V_H$ to the N-terminus of $V_L$, or (2) the C-terminus of $V_L$ to the N-terminus of $V_H$. A 15-mer (Gly$_4$Ser)$_3$ peptide may be used as a linker, but other linkers are known in the art. These antibody fragments are obtained using conventional techniques known to those with skill in the art, and the fragments are evaluated for function in the same manner as are intact antibodies.

The term "elongated region" refers to a section of the complex formed by the target analyte and the first and second probes that is sufficiently long such that when the complex tethers a particle to a solid support the displacement of the particle can be detected and differentiated from the displacement of particles that are non-specifically attached to the solid support. In preferred embodiments, the elongated region is a biomolecule, such as a polysaccharide, polypeptide or nucleic acid, between about 0.15 and about 20 μm long. In even more preferred embodiments, the elongated region is a double stranded nucleic acid, between about 0.5 and about 5 μm long.

The terms "test sample" or "sample" are used interchangeably herein and include, but are not limited to, biological samples that can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like, biological fluids such as cell culture supernatants, fixed tissue specimens and fixed cell specimens, PCR amplification products or a purified product of one of the above samples. A "sample" may include gaseous mediums, such as ambient air, chemical or industrial intermediates, chemical or industrial products, chemical or industrial byproducts, chemical or industrial waste, exhaled vapor, internal combustion engine exhaust, or headspace vapor such as vapor surrounding foods, beverages, cosmetics, vapor surrounding plant or animal tissue and vapor surrounding a microbial sample. Another example of "sample" relevant to this invention is a liquid solution produced by dissolving material collected by filtering a gaseous sample or a liquid solution produced by exposing the liquid to a gaseous sample. Additional sample mediums include supercritical fluids such as supercritical $CO_2$ extricate. Other exemplary mediums include liquids such as water or aqueous solutions, oil or petroleum products, oil-water emulsions, liquid chemical or industrial intermediates, liquid chemical or industrial products, liquid chemical or industrial byproducts, and liquid chemical or industrial waste. Additional exemplary sample mediums include semisolid mediums such as animal or plant tissues, microbial samples, or samples containing gelatin, agar or polyacrylamide.

The term "solid support" is used herein to denote any solid material suitable for coupling to a probe and which is amenable to the detection methods disclosed herein. The number of possible suitable materials is large and would be readily known by one of ordinary skill in the art.

The term "particle" is used to indicate any solid object or fluorescent molecule suitable for coupling to a probe and which is amenable to the detection methods disclosed herein.

The term "surface" or "surfaces" is used to indicate the external layer of the solid support and the particles.

In exemplary embodiments, the solid support or the particles may be composed of modified or functionalized glasses, inorganic glasses, plastics, including acrylics, polystyrene and copolymers of styrene, polypropylene, polyethylene, polybutylene, polyurethanes, Teflon, polysaccharides, nylon or nitrocellulose, resins, and other polymers, carbon, metals, ceramics, silica or silica-based materials including silicon and modified silicon and silicon wafers. In aspects, the surface can be a composite material.

Surfaces can be functionalized with molecules by physical or chemical adsorption. In preferred embodiments, the surfaces are functionalized with probes or with molecules capable of coupling to probes. Such methods of functionalization are known in the art. For instance, a gold surface can be functionalized with nucleic acids that have been modified with alkanethiols at their 3'-termini or 5'-termini. See, for example, Whitesides, Proceedings of the Robert A. Welch Foundation 39th Conference On Chemical Research Nanophase Chemistry, Houston, Tex., pages 109-121 (1995). See also Mucic et al., Chem. Commun. 555-557 (1996) (describes a method of attaching 3' thiol DNA to flat gold surfaces; this method can be used to attach oligonucleotides to nanoparticles). The alkanethiol method can also be used to attach oligonucleotides to other metal and semiconductors. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, Chemical Technology, 4, 370-377 (1974) and Matteucci and Caruthers, J. Am. Chem. Soc., 103, 3185-3191 (1981) for binding of oligonucleotides to silica and glass surfaces, and Grabar et al., Anal. Chem., 67, 735-743 for binding of aminoalkylsiloxanes and for similar binding of mercaptoaklylsiloxanes). Oligonucleotides terminated with a 5' thionucleoside or a 3' thionucleoside may also be used for attaching oligonucleotides to solid surfaces. Another example of surface functionalization that is important for the present invention is the immobilization of antibodies and other binding members to the surface either by physical adsorption or by direct or indirect chemical linkage. For instance, surfaces can be functionalized by chemically linking streptavidin molecules to them, which are capable of coupling to probes comprising one or more biotin molecules. The following reference describes the attachment of biotin labeled oligonucleotides to a streptavidin functionalized surface. Shaiu et al., Nucleic Acids Research, 21, 99 (1993). Digoxigenin and anti-Digoxigenin antibodies can also be used to attach probes to surfaces.

The surfaces can be functionalized by a monolayer of one or more molecules. Methods of producing self-assembled monolayers are well known in the art. In particular, there are several known methods to assemble monolayers of thiolates on metal surfaces. See e.g., Love, J. C. et al., Chem. Rev., 105, 1103 (2005).

The surface functionalization methods described above can be used to couple molecules that prevent or reduce non-specific interactions with the surface. For instance, after immobilization on to the surface of an analyte binding molecule, such as a ssDNA or an antibody, physical adsorption on the surface of a protein that blocks non-specific interactions is often conducted. Common proteins used as blockers are: bovine serum albumin (BSA), fish serum and milk proteins, such as casein.

The following references describe other methods that may be employed to attach oligonucleotides to surfaces: Nuzzo et al., J. Am. Chem. Soc., 109, 2358 (1987) (disulfides on gold); Allara and Nuzzo, Langmuir, 1, 45 (1985) (carboxylic acids on aluminum); Allara and Tompkins, J. Colloid Interface Sci., 49, 410-421 (1974) (carboxylic acids on copper); Iler, The Chemistry Of Silica, Chapter 6, (Wiley 1979) (carboxylic acids on silica); Timmons and Zisman, J. Phys. Chem., 69, 984-990 (1965) (carboxylic acids on platinum); Soriaga and Hubbard, J. Am. Chem. Soc., 104, 3937 (1982) (aromatic ring compounds on platinum); Hubbard, Acc. Chem. Res., 13, 177 (1980) (sulfolanes, sulfoxides and other functionalized solvents on platinum); Hickman et al., J. Am. Chem. Soc., 111, 7271 (1989) (isonitriles on platinum); Maoz and Sagiv, Langmuir, 3, 1045 (1987) (silanes on silica); Maoz and Sagiv, Langmuir, 3, 1034 (1987) (silanes on silica); Wasserman et al., Langmuir, 5, 1074 (1989) (silanes on silica); Eltekova and Eltekov, Langmuir, 3, 951 (1987) (aromatic carboxylic acids, aldehydes, alcohols and methoxy groups on titanium dioxide and silica); Lec et al., J. Phys. Chem., 92, 2597 (1988) (rigid phosphates on metals).

As used herein, a "detectable signal" which can be generated according to the invention includes, but is not limited to, an electrical, mechanical, optical, acoustic or thermal signal. In preferred embodiments, the detectable signal is optical or electrical.

As used herein, a "polymer" is a molecule formed by monomers in which each monomer is covalently linked to other monomers.

The term "monomer" is used herein to refer to a molecule that has the ability to combine with identical or other molecules in a process known as polymerization. The polymerization reaction may be a dehydration or condensation reaction (due to the formation of water ($H_2O$) as one of the products) where a hydrogen atom and a hydroxyl (—OH) group are lost to form $H_2O$ and an oxygen molecule bonds between each monomer unit.

The term "monomer" includes any chemical group that can be assembled into a polymer. A wide variety of monomers may be used for synthesizing a polymer. For example, a polymer of the invention may be composed of monomers that have hydrophilic groups, and/or hydrophobic groups pendant from their backbones. Accordingly, a polymer may include side chains "R" pendant from a structurally repetitive backbone. Exemplary backbones with side chains include:

—(CO—N(—R)—CH$_2$)—;

—(O—Si(—CH$_3$)(—R))—;

—(CH$_2$—CH(—R)—CO—NH)—;

—(CH$_2$—CH(—R)—O)—; and

—(CH$_2$—C$_6$H$_4$—CO—N(—R))—.

—(CH$_2$—CHR)—, or —(CH$_2$—CH$_2$—CHR)—;

—(CF$_2$—CFR), or —(CF$_2$—CF$_2$—CFR)—; and

—(CH$_2$—CH(—CO—NHR))—.

Examples of polymers suitable for use in this invention are polyethylene oxide (PEO), polyethylene glycol (PEG), polyisopropylacrylamide (PNIPAM), polyacrylamide (PAM), polyvinyl alcohol (PVA), polyethylenimine (PEI), polyacrylic acid, polymethacrylate and polyvinylpyrrolidone (PVP) polyvinyls, polyesters, polysiloxanes, polyamides, polyurethanes, polycarbonates, fluoropolymers, polyethylene, polystyrene, polybutadiene, polydimethylsiloxane (PDMS), polypropylene, polymethylmethacrylate, polytetrafluoroethylene and polyvinyl chloride (PVC).

Additional examples of suitable polymers include, but are not limited to, those described in the references cited in this written description and incorporated by reference herein. Nomenclature pertinent to molecular structures, as well as description of monomers and side chain structures useful for the present invention can be found in U.S. Patent Publication No. U.S. 2009/0011946, which is hereby incorporated by reference in its entirety.

As used herein, the term "polysaccharides" refers to polymeric carbohydrate structures, formed of repeating units (either mono- or di-saccharides) joined together by glycosidic bonds. Polysaccharides of the invention are preferably linear, but may contain various degrees of branching. Additionally, polysaccharides are generally heterogeneous, containing slight modifications of the repeating unit. Examples of polysaccharides suitable for the invention include homopolysaccharides or homoglycans, where all of the monosaccharides in a polysaccharide are the same type, and heteropolysaccharies or heteroglycans, where more than one type of monosaccharide is present. In exemplary embodiments, the polysaccharide is a starch, glycogen, cellulose, or chitin.

Polysaccharides of the invention have the general formula of $C_x(H_2O)_y$. In some embodiments, X is about 100 to about 100,000, about 200 to about 10,000, about 500 to about 5,000, or about 1,000 to about 2,000. In another embodiment, polysaccharides have repeating units in the polymer backbone of about six-carbon monosaccharides and can be represented by the general formula of $(C_6H_{10}O_5)_n$ where n is about 30 to about 100,000, about 200 to about 10,000, about 500 to about 5,000, or about 1,000 to about 2,000.

As used herein, the terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA") or RNA/DNA hybrids. It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, siRNA, and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic nucleic acid polymers providing that the polymers contain nucleobases in a configuration which allows for base pairing and base stacking, such as is found in DNA and RNA. The term nucleotides include hybrids thereof, for example between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine and psoralen), those containing chelates (e.g., metals, radioactive metals, boron, oxidative metals, etc.), those containing alkylators, those with modified linkages (e.g., alpha anomeric nucleic acids, etc.).

Oligonucleotides of defined sequences are used for a variety of purposes in the practice of the invention. Methods of making oligonucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

As used herein, the term "polypeptides" refers to a polymer formed from the linking, in a defined order, of preferably, α-amino acids, D-, L-amino acids and combinations thereof. The terms "peptides," "oligopeptides," and "proteins" are included within the definition of polypeptide. The term includes polypeptides containing post-translational modifications of the polypeptide, for example, glycosylations, acetylations, phosphorylations, and sulphations. In addition, protein fragments, analogs (including amino acids not encoded by the genetic code, e.g. homocysteine, ornithine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide. The link between one amino acid residue and the next is referred to as an amide bond or a peptide bond. The terms do not refer to a specific length of the polypeptide.

In some embodiments, the elongated region of one or both probes comprise a non-biological hydrophilic polymer, such as polyethylene oxide (PEO), polyethylene glycol (PEG), polyisopropylacrylamide (PNIPAM), polyacrylamide (PAM), polyvinyl alcohol (PVA), polyethylenimine (PEI), polyacrylic acid, polymethacrylate and polyvinylpyrrolidone (PVP), or a combination thereof.

In preferred embodiments, the elongated region of one or both probes and/or the target analyte comprises a biomolecule, such as a polysaccharide, polynucleotide, or a polypeptide, or a combination thereof.

A preferred embodiment is a method of detecting a target analyte in a sample. In this method, a complex is provided, the complex formed from: a first probe coupled to a particle and bound to said analyte if present, and a second probe coupled to a solid support and bound to said analyte if present, so that if the target analyte is present in the sample, the particle is indirectly coupled to the solid support via a complex formed by the target analyte and the first and second probes, and wherein the complex comprises an elongated region. It will be understood that the provided complex may have been formed in any possible manner and order of steps. It will also be clear that the person(s) who carries out any of the complex-formation steps may, but need not be, the person who performs the subsequent steps in the process, i.e., applying the force or measuring the Brownian motion.

Preferably, the first probe, the second probe, and the target analyte comprise nucleic acids or oligonucleotides. More preferably, the first probe and second probe each comprise a region for binding the target analyte. The first probe couples to a particle at a different location than where the target analyte binds to the first probe. The second probe couples to the solid support at a different location than where the target analyte binds to the second probe. The complex formed by the target analyte and the first and the second probe comprises an elongated region. In a preferred embodiment, the elongated region of the complex formed by the target analyte and the first and the second probe comprises double-stranded DNA having a total length ranging from about 500 base pairs to about 60,000 base pairs, for example, from about 1,500 base pairs to about 15,000 base pairs.

In preferred embodiments, if the target analyte is a nucleic acid, the nucleic acid target can form base pairs with unpaired nucleotides in the first probe and with unpaired nucleotides in the second probe. In an aspect of this embodiment, the first probe further comprises a region for coupling to the particle. For example, the first probe can comprise a protein, a peptide, or an antigen covalently attached to the 5' or 3' end of a nucleic acid.

In another preferred aspect, the target analyte is not a nucleic acid. When the target analyte is not a nucleic acid, the first and second probes preferably comprise an antibody.

In yet another preferred aspect, the target analyte is a nucleic acid and the first and second probes bind to locations on the target that are at least 500 nucleotides from each other. According to this aspect the target can be either double or single stranded. When the target is single stranded, the force required to extend it is significantly higher than the force required to extend a double stranded nucleic acid (Current Opinion in Structural Biology 2000, 10:279; Nucleic Acids Research 2014 (42), 3:2064). The force required to extend the single stranded nucleic acid can be modified by changing solution properties, such as ionic strength and temperature, and/or adding a molecule that bind to the single strand.

When the target analyte is a nucleic acid molecule, exposure of the target analyte to the first and/or second probe is preferably conducted under high stringency conditions. High stringency conditions favor the hybridization of nucleic acid molecules which are perfectly complementary or substantially perfectly complementary to single stranded nucleic acids in the probe and make more unlikely the binding of targets which are not perfectly complementary or substantially perfectly complementary. After exposure of the target solution to the first and/or second probe, washing or exposing the probes to a medium with high stringency can remove non-perfectly complementary molecules as well. High stringency conditions occur at high temperature, low salt concentration and high pH. Also the presence of certain chemicals, such as formamide, can increase the stringency of the solution. In an embodiment, exposure of the target to probes and washing, when performed, are conducted preferably at temperatures between 20° C. and 70° C., ionic strength between 0.01 M and 1 M, and pH between 7 and 8.

Some methods of this invention contain "exposing" steps where the probe(s), particles, and/or solid support are exposed to the sample or one another. These exposing steps can occur in any order, or even simultaneously. For example, in one embodiment, reactants are exposed in the following order, before applying force to the particle and measuring displacement: a) the first and second probe are exposed to the target analyte, b) the second probe which comprises a first end for coupling to the solid support, is exposed to the solid support, c) the first probe which comprises a first end for coupling to the particle is exposed to the particle. If these steps are conducted under conditions that allow reactants to bind or couple and if the target analyte is present in the sample, the particle is indirectly coupled to the solid support via a complex formed by the target, and the first and second probes. However, in another embodiment of the present invention, the steps are conducted in reverse order (c-b-a). If these steps are conducted under conditions that allow reactants to bind or couple and if the target analyte is present in the sample, the particle is indirectly coupled to the solid support as before: via the first probe, the target analyte and the second probe. In another exemplary embodiment all the steps can be conducted simultaneously. If this single step is conducted under conditions that allow reactants to bind or couple and if the target analyte is present in the sample, the particle is indirectly coupled to the solid support in the same manner as the previous two examples: via the first probe, the target analyte and the second probe. Any order and/or combination of steps that are conducted simultaneously will have the same result, if each step is conducted under conditions that allow reactants to bind or couple.

In preferred embodiments, the particle is a solid bead with a diameter between about 0.1 µm and about 20 µm, or between about 0.3 µm and about 5 µm. Preferred bead materials are: silica-based glasses, such as quartz and borosilicate; zirconium and organic polymers, such as polystyrene, melamine resin and polyacrylonitrile.

In preferred embodiments, the particle is a superparamagnetic bead with a diameter between about 0.5 µm and about 5 µm. Superparamagnetic beads are commonly used in biotechnological applications. They consist of a polymer matrix that contains small (<about 10 nm) particles of a ferromagnetic material in it. The small size of the ferromagnetic particles makes them superparamagnetic. As a result, the beads are magnetic only under the influence of an external magnetic field.

In some embodiments, the particle is a quantum dot. A quantum dot is typically less than about 10 nm and made of semiconductor materials that display quantum mechanical properties. As a result of these properties, the electronic characteristics of quantum dots are related to the size and shape of the individual crystal. Quantum dots are fluorescent and the emission frequency increases as the size of the quantum dot decreases. Therefore the color of quantum dots can be controlled by their size.

In some embodiment, the particle is a nanorod. Preferably, the length of the nanorods is at least about 0.5 µm. Methods of making nanorods or nanowires are known in the art. See for example, Hahm and Mieber, Nano Lett, 4, 51-54 (2004) (silicon nanorods); Li et al., Appl. Phys. Lett. 4, 4014-1016 (2003) (In203 nanorods); Liu et al., Phys. Ev. B. 58, 14681-14684 (1998) (Bismuth nanorods); Sun et al., Appl. Phys. Lett. 74, 2803 (1999) (Nickel nanorods); Ji et al., J. Electrochem. Soc. 150, C523-528 (2003) (Au/Ag multilayers and multisegment nanorods); Celedon et al., Nano Lett., 9, 1720-1725 (2009) (Pt/Ni multisegment nanorods); O'Brien et al., Adv. Mater. 18, 2379-2383 (2006) (polymer nanorods); Liu et al. Nanotechnology 20, 415703 (2009) (superparamagnetic and ferromagnetic Ni nanorods).

In some embodiments, the particle comprises a fluorescent molecule. These molecules are known to those skilled in the art. For example, a fluorescent nucleic acid can be created in a PCR reaction where one of the deoxynucleotides in the reaction mix has a florescent label. A commonly used labeled deoxyadenosine triphosphate for this procedure is Fluorescein-12-dATP. Protocols to label nucleic acid molecules are readily available (Nucl. Acids Res. (1994) 22 (16):3418; Nat Biotechnol. (2008) 26(3):317; Nat Biotechnol. (2000) 18 (2):233). Another example of fluorescent molecule is a single fluorophore, such as Cy3 and other cyanines, and fluorescein.

In some embodiments, the probes and/or target may be labeled before or after the application of force with at least two particles, one particle at one end of the probe-target complex, the other at the other end. In one embodiment, the elongated region of the complex may be labeled substantially along its length with fluorescent molecules. For example, the elongated region may be a double stranded DNA that is labeled with a nucleic acid fluorescent dye, such as YOYO-1. The approximate length of the elongated region can be determined from the position of said particles after the application of force. In these embodiments the discrimination of non-specific interaction is based on the length of the elongated region. If the full length of the elongated region is observed, it means that the target analyte is present. Instead, if a fraction of the length of the elongated region is observed, it means that the attachment to the solid support is via non-specific interactions.

One embodiment of the invention is shown in FIG. 1A. According to this embodiment, the first probe and second probes are exposed to a sample comprising the target analyte. After the target analyte binds to both the first and second probes, particles are introduced into the sample, which couples to the first probe. After the particle couples to the second probe, the sample is exposed to a solid support, where the second probe is coupled to the solid support. As explained elsewhere, the order of exposing the probe to the sample, the solid support and/or the particles can vary. Thus, for example, the particle can be exposed to the first probe prior to exposure of the target analyte to the first and second probe.

Figure 1B:
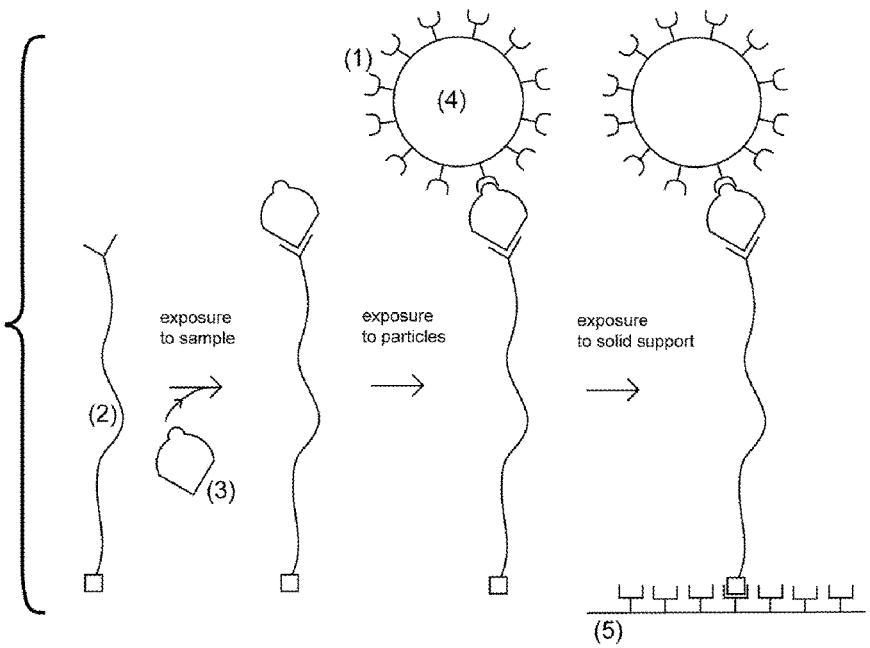
FIG. 1B depicts an embodiment wherein the second probe comprising an elongated region (2) is exposed to a sample under conditions such that if the target analyte (3) is present in the sample then it binds to the second probe (2). Upon exposure of a particle (4) coupled to the first probe (1) to the sample, the first probe (1) binds to the target analyte (3). Upon exposure to a solid support (5), the second probe (2) couples to the solid support (5).

Another embodiment of the invention is shown in FIG. 1B. According to this embodiment, the second probe is exposed to a sample comprising the target analyte. The second probe comprises an antibody specific for the target analyte. After the target analyte binds to the probe, particles are introduced into the sample. The particles are functionalized with a first probe that comprises an antibody specific for the target analyte. After the first probe binds to the target analtye, the sample is exposed to a solid support, where the second probe is coupled to the solid support. As explained elsewhere, the order of exposing the probe to the sample, the solid support and/or the particles can vary. Thus, for example, the first probe can be exposed to the target analyte prior to exposure of the target analyte to the second probe.

Figure 2A:
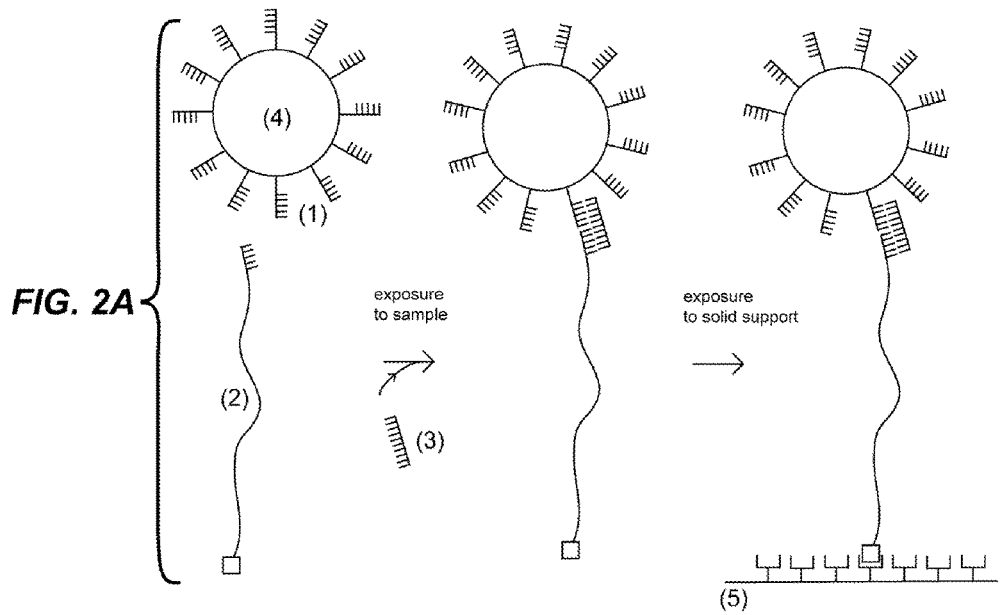
FIG. 2A depicts an embodiment wherein the first probe (1) coupled to a particle, and the second probe comprising an elongated region (2) are exposed to a sample under conditions such that if the target analyte (3) is present in the sample then it binds to the first probe (1) and to the second probe (2). Upon exposure to a solid support (5), the second probe (2) couples to the solid support (5).
Figure 2B:
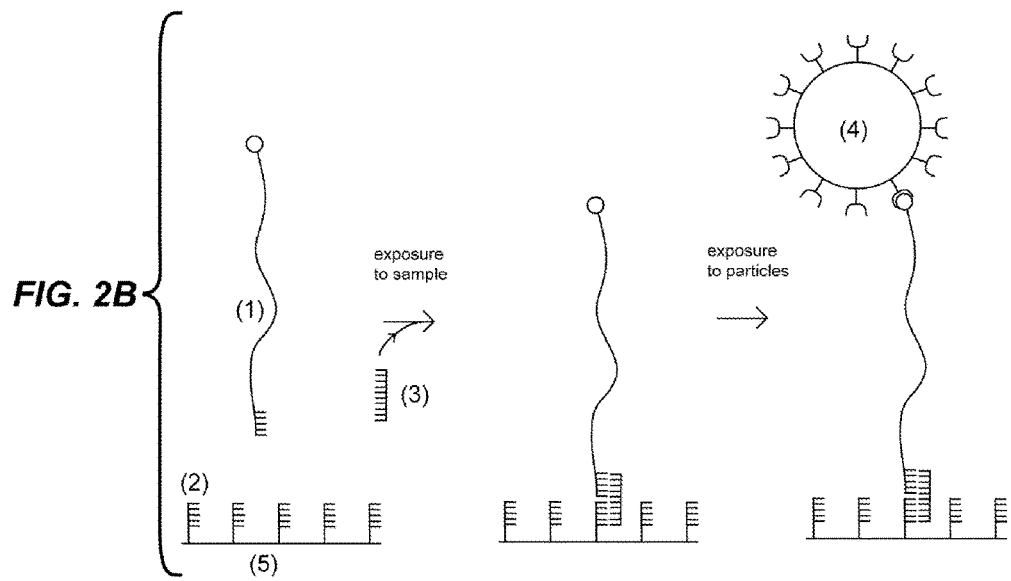
FIG. 2B depicts an embodiment wherein the second probe (2) coupled to a solid support (5) and first probe comprising an elongated region (1) are exposed to a sample under conditions such that if the target analyte (3) is present in the sample then it binds to the first probe (1) and to the second probe (2). Upon exposure to a particle (4), the particle (4) couples to the first probe (1).

Other embodiments of the invention are shown in FIG. 2. According to these embodiments, the analyte comprises a nucleic acid and the probes comprise a nucleic acid. One probe comprises a first end or region for coupling to either the particle or the solid support and a second end or region for binding to the analyte, and either the particles or the solid support comprise a second analyte binding region. In one embodiment (FIG. 2A), the first probe (1) is covalently attached to the surface of a particle (4). After the target analyte (3) binds to the first (1) and second (2) probes, the sample is exposed to a solid support (5), where the second probe (2) is coupled to the solid support. As explained elsewhere, the order of exposing the probe to the sample, the solid support and/or the particles can vary. In another embodiment (FIG. 2B), the second probe (2) is a nucleic acid coupled to the solid support (5). The target analyte (3) can be exposed to the first probe (1) prior to exposure of the target analyte (3) to the second probe (2) or, alternatively, the target analyte can be exposed to the second probe (2) prior to exposure of the target analyte (3) to the first probe (1). In yet another alternative, the target analyte can be exposed to the probe and solid support simultaneously. After the target analyte binds to both the first and second probes, particles are introduced to the sample, where a particle couples to the first probe. Alternatively, the first probe can be coupled to the particle prior to exposure to the sample and/or prior to exposure to the second probe.

Figure 4:
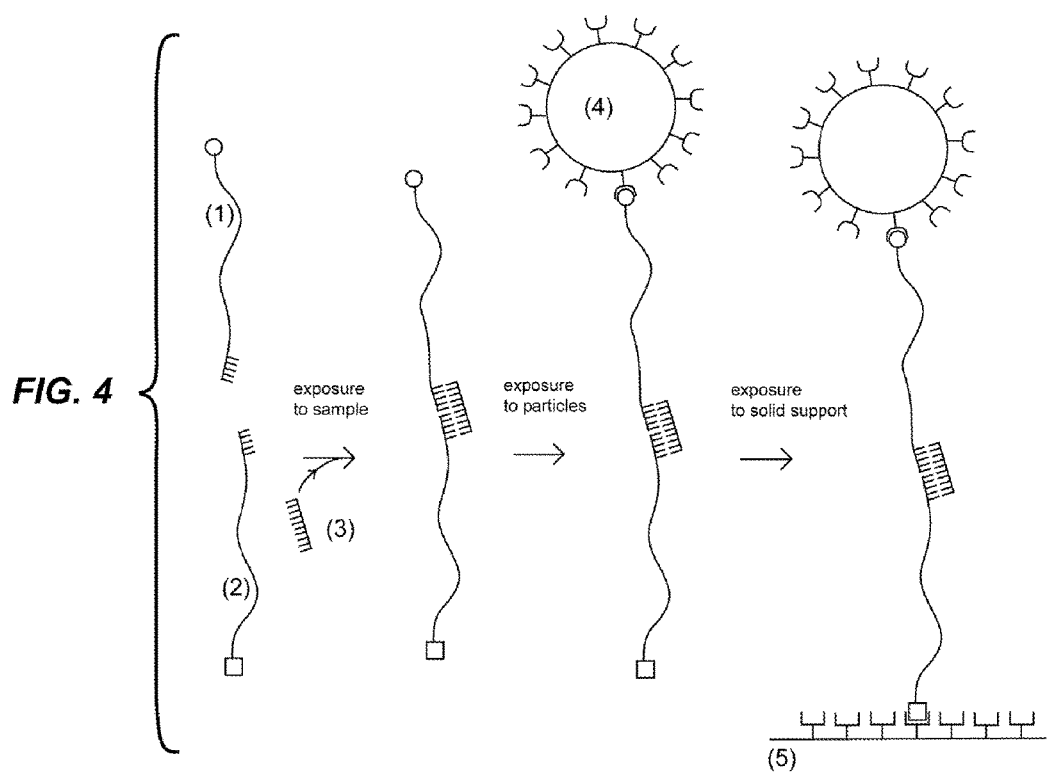
FIG. 4 depicts an embodiment wherein the first probe comprising an elongated region (1) and the second probe comprising an elongated region (2) are exposed to a sample under conditions such that if the target analyte (3) is present in the sample then it binds to the first probe (1) and the second probe (2). Upon exposure of a particle (4) to the sample, the particle (4) couples to the first probe (1). Upon exposure to a solid support (5), the second probe (2) couples to the solid support (5).

Another embodiment of the invention is shown in FIG. 4. According to this embodiment, the first (1) and second (2) probes are exposed to a sample comprising the target analyte (3). The target analyte can be exposed to the first probe prior to exposure of the target analyte to the second probe or, alternatively, the target analyte can be exposed to the second probe prior to exposure of the target analyte to the first probe. In yet another alternative, the target analyte can be exposed to the first and second probes simultaneously. After the target analyte binds to both the first and second probes, particles (4) are introduced into the sample, which couple to the first probe. After the particle couples to the first probe, the sample is exposed to a solid support (5), where the second probe is coupled to the solid support. Alternatively, the particle can be exposed to the first probe prior to exposure of the target analyte to the first and second probe.

Figure 3:
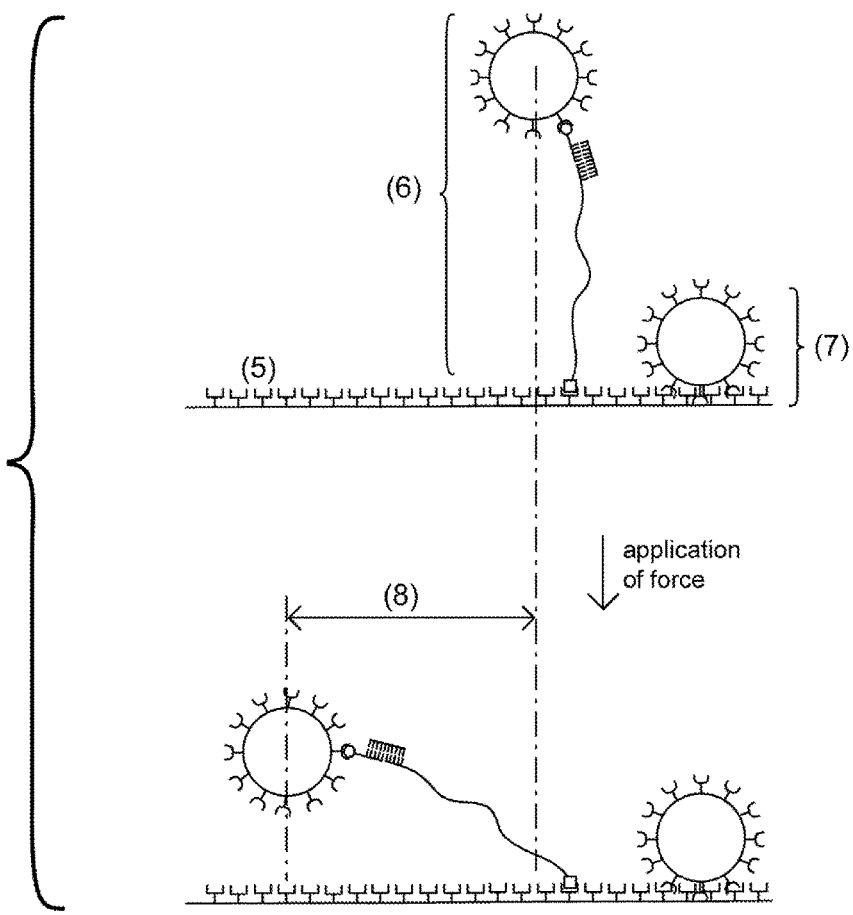
FIG. 3 depicts the effect of the application of force on particles attached to a solid support. If a particle is attached to the solid support via a complex that comprises an elongated region (as shown at (6)), the particle moves a distance (8) that is a function of the length of the probe. If the particle is non-specifically bound to the solid surface (as shown at (7)), the particle does not move or moves a distance significantly less than the specifically-bound particle (6).

In an aspect according to some of the embodiments, a force is applied to the particles. The force field acts on the particle and pulls it away from its initial position (e.g. a magnetic field acting on a magnetic particle or a flow exerting a drag on a particle). The device is exposed to a sample in conditions such that if the target analyte is present, then a complex is formed by the target analyte and the first and second probes. Consequently, when a force is applied, the particle that is associated with the complex will move a distance that is a function of the length of the complex. As shown in FIG. 3, this amount of displacement (8) indicates specific binding. Correspondingly, the particles that are non-specifically bound (7) to the solid support will move a shorter distance, if at all, than the specifically-bound particles.

In one embodiment, the detection device is exposed to the sample in conditions such that the number of beads tethered by probes is proportional to the concentration of the target analyte. In this manner, the detectable signal is proportional to the concentration of the target analyte, thereby permitting the concentration of the target analyte in the sample to be determined.

Preferred embodiments use probes having elongated regions of multiple different lengths, with each probe of a certain length having a region capable of binding a specific target analyte, in such a manner that each probe length is associated with a different target analyte. In this embodiment, the approximate concentration of multiple target analytes in a sample can be determined in a single assay by measuring different displacements of particles after application of force, grouping them based on the amount of displacement and counting the number of particles associated with each possible displacement.

In related embodiments, the multiplexing capability is further increased by modifying the probes having elongated regions in such a manner that each of them may have more than one length and the change of length is triggered by an external agent. Examples of external agents that can trigger a change of length are temperature, ionic strength, pH, force, an auxiliary molecule, such as a nucleic acid, an enzyme a detergent, etc. In these embodiments, the identity of a target is determined after measuring the displacement of the particle before and after triggering the change of length. The change of length can be triggered multiple times. For example, in an assay with 100 different probes having an elongated region, each probe specific to a different target analyte can be created by a set of probes that have 10 different lengths before triggering the length change and wherein each probe experiences one out of 10 possible different length changes upon triggering the length change. An example of a probe with an elongated region having a length that can be changed by an external agent is a probe in which two remote positions in the probe interact in such a manner that an internal loop is formed. In this case, the external agent can trigger the release or the formation of an internal loop. The characteristics of the external agent required to trigger the change of length are controlled by the characteristics of the interaction. For example, if the interaction is the hybridization between nucleic acid molecules, the specific sequence can be used to modulate the characteristics of the triggering agent. An example of an external agent that can trigger the release of an internal loop formed by hybridization between nucleic acid molecules is an auxiliary nucleic acid complementary to one of the molecules in the hybridization region that holds an internal loop. When the probe is exposed to this auxiliary nucleic acid, the auxiliary nucleic acid can displace one of the strands in the hybridization region, thereby releasing the loop. Another example of an external agent is an auxiliary nucleic acid that has a first and a second region, wherein the first region is complementary to a first region in a nucleic acid probe and the second region is complementary to a second region in the probe. When the probe is exposed to this nucleic acid, the nucleic acid binds to the two regions in the probe which produces an internal loop. In related embodiments, the auxiliary molecules are proteins that can be used similarly to the nucleic acid described above with the purpose of releasing or forming internal loops.

The surfaces and probes of the present invention may have a plurality of different analyte binding molecules attached to them, and as a result, the tethering of beads to the solid support could be triggered by a plurality of target analytes.

In one embodiment, a solid support may have an array of regions, each region comprising a second probe specific to a unique target molecule. Thus, exposure of the solid support to the sample captures different targets at different locations in the array. Therefore, detection of particle displacement in a specific array region indicates that the corresponding target molecule is present in the sample. According to this embodiment, a method is provided for creating a unique profile or fingerprint of a sample having any number of different target analytes (e.g., any of two through one thousand, or even more). As such, profiles from different samples can be stored in a database and/or compared for diagnostic purposes for the detection of diseases or disorders.

Another embodiment uses multiple distinguishable particles, wherein each different particle comprises a different first probe specific to a different molecule. For example, fluorescent beads of different colors are functionalized with different antibodies, one antibody kind for each bead color. In this manner, the specific target molecules present in the sample are identified by detecting the color of the tethered beads that are displaced under a force. Alternatively, beads of different sizes or distinguishable strings of fluorescent molecules or particles can be used (Nat. Biotech. 26, 317-325, 2008).

In a preferred aspect of some of the embodiments, the applied force is fluid drag. This type of force is generated by the flow of the liquid solution in which the particle and/or molecule is immersed. More precisely, this force is applied when there is a difference between the speed of the liquid and the speed of the particle and/or molecule. This force is normally parallel to the solid support, but it can have a component perpendicular to the solid support if the solid support is porous. In preferred embodiments, the particles are in proximity to the surface of the solid support and the flow is substantially parallel to the surface of the solid support. In these embodiments, the speed of the fluid increases away from the surface of the solid support and not only produces a linear force substantially parallel to the surface of the solid support but also a torque. The terms "fluid drag" and "fluid drag force" are used to indicate the combination of both the linear force and torque, when it exists, experienced by the particles. In preferred embodiments, the particles have a diameter or length less than about 20 micrometers and the flow is laminar, with a Reynolds number less than about 1. Typically, the particles and/or molecule are inside a capillary tube and flow can be generated using a pump, such as a syringe pump, connected to the capillary by a hose. Another way of generating a suitable flow is to exert an external pressure on the hose connected to the capillary. The pressure moves a small amount of fluid into the capillary, which displaces the particles away from the side of the capillary where the pressure was applied. Releasing the pressure in the hose displaces the beads in the opposite direction.

In an aspect of some of the embodiments, the applied force on the particle is fluid buoyancy. This type of force is equal to the weight of the fluid displaced by the particle and in the direction opposite to the gravitational force.

In an aspect of some of the embodiments, the applied force is a magnetic force. In these embodiments, the particles are magnetic, such as superparamagnetic beads. The force is a consequence of the presence of a magnetic field which can be generated with permanent magnets, such as iron or rare earth magnets, or electromagnets. The magnetic force can be used to pull the particles away from the glass surface, in such a way that particles tethered via an elongated region are displaced to a plane higher than the particles non-specifically attached to the surface. This type of displacement can be detected optically using an imaging system able to image planes parallel to the solid support. In this imaging system, this type of displacement produces a change in diffraction pattern when the particle moves to a different focal plane. Alternatively, the magnetic force can be used to pull the particles in a direction parallel to the surface of the solid support. This type of displacement is easily detected as a change of position of the particles in the image using an optical system.

In another aspect of some of the embodiments, the applied force is gravitational. In these embodiments the direction of the force is always toward the center of the earth and therefore its direction with respect to the solid support is determined by the orientation in space of the solid support.

In another aspect of some embodiments, the applied force is centrifugal. In these embodiments, the particles are subjected to a motion that changes direction. Preferably, the motion is a rotational motion.

In another aspect of some of the embodiments, the applied force is electrical. An electrical force is generated when at least two electrodes having different voltage are introduced in the solution generating a voltage gradient.

In another aspect of some of the embodiments, the force is applied to the target-probe complex using flow, a receding meniscus, or a voltage gradient.

In another embodiment, the formed complex is coupled to a substantially flat solid support, and is subjected to a force substantially parallel to the solid support. In that embodiment, the force is selected such that it removes non-specifically bound particles from the support. Then, using suitable detection methods, the presence of remaining particles indicates the presence of the target analyte in the sample.

Figure 8A:
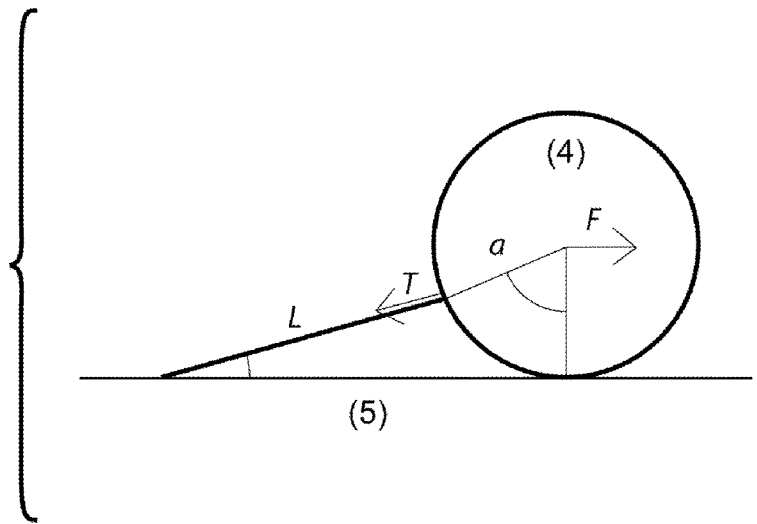
FIG. 8A depicts a spherical particle (4) of radius a tethered to the solid support (5) by a tether of length L. The particle experiences an horizontal force parallel to the surface of the solid support (F) which induces a tension on the complex (7).
Figure 8B:
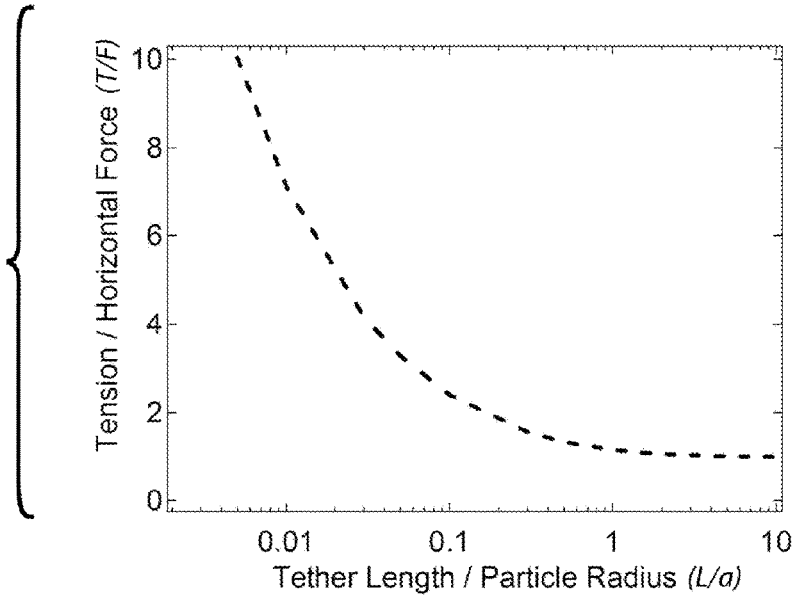
FIG. 8B depicts the ratio of the tension and horizontal force (T/F) as a function of the ratio of tether length and particle radius (L/a) for the physical situation depicted in FIG. 8A.

In embodiments that use a force substantially parallel to the solid support, such as embodiments that apply fluid drag substantially parallel to the solid support, force can remove non-specifically bound particles while not significantly reducing the signal because being part of a complex with an elongated region reduces the force experienced by the target analyte. When force substantially parallel to the solid support is applied on particles bound to the solid support, the tension on the tether decreases with tether length (Langmuir 1996, 12(9): 2271). Therefore, non-specific interactions, which are normally tethers about 10 nanometers long, experience tensions that are significantly higher than the tension that a target bound in an elongated complex experience. This property of long tethers allows in embodiments of the present invention the removal of non-specifically bound particles without significantly affecting specifically bound particles. Using complexes comprising an elongated region larger than the non-specific tethers present in a particular assay improves the selective removal of non-specifically bound particles in that assay. If the tethered particle is a sphere of radius a touching the solid support that experiences a force parallel to the solid support, as shown in FIG. 8A, then the tension (T) in the tether (length L) as a function of the horizontal force (F) can be calculated by balancing forces and torques. FIG. 8B shows the value of the ratio of tension and horizontal force (T/F) as a function of the ratio of tether length and particle radius (L/a). The tension in the tether dramatically increases for tether lengths that are less than half the radius of the particle. For example, for a tether that is 0.01 times the radius of the particle, the tension is 7 times higher than the horizontal force, while for a tether that is 2 times the radius of the particle, the tension is only 6% higher than the horizontal force. In embodiments that apply fluid drag substantially parallel to the solid support, the torque applied on the particle by the drag further increases the difference in the tension experienced by short versus long tethers.

The application of force to the complex formed by the target analyte and the first and second probes either directly or indirectly through force applied to the particle can increase the target specificity of the detection system by removing complexes where the target is not the exact binding partner of the binding regions in the probes. When the target is a nucleic acid, this situation takes place, in most cases, when the target is not perfectly complementary to a nucleic acid region in the probes. The application of force is a novel form of hybridization stringency. This stringency can be modulated by the configuration of the structure formed by probes when they bind to the target. In particular for nucleic acids, a probe can hybridize to a target in two main types of configurations. In a first configuration, the axis of the duplex is in the direction of the force and the application of force tends to disrupt all the base pairs simultaneously. In a second configuration, the axis of the duplex is perpendicular to the direction of the force and the application of force tends to disrupt base pair in a progressive order, starting with the ones closer to the point of force application. The stringency can be modulated by the amount of force applied (Current Opinion in Chemical Biology 2008, 12: 640, PNAS 2006 (103), 16:6190).

The term "coiling" as used herein refers to a conformational change suffered by bundles of two or more polymers subjected to a rotational force. A simple example of "coiling" takes place when two linear polymers are held together by holding a first end from each polymer together at one location and a second end of the polymers together at a second location, if the second end of one polymer rotates around the second end of the other polymer, the two polymers will wind around each other. As rotations accumulate the two polymers will start presenting a more compact conformation. This phenomenon is referred in the present invention as "coiling". Another example of coiling is "supercoiling". In this case, two or more nucleic acid strands are connected by base pairing and in the absence of torsional stress wind around each other. "Supercoiling" takes place when the strands are either winded or unwinded from their natural amount of winding. "Supercoiled" structures have writhe (PNAS 1978, 75 (8) 3557).

In some embodiments, the present invention may be incorporated into an assay as described in: International Patent Publication WO 2013/059044 published Apr. 25, 2013 and entitled "Detection Units and Methods for Detecting a Target Analyte", United States Patent Application Publication US 2014/0099635 A1 published Apr. 10, 2014 and U.S. Provisional Application 61/983,684, filed on Apr. 24, 2014, the contents of these publications are incorporated by reference herein. In some of these embodiments, and referring to present FIG. 5A, the particle may be a magnetic particle (4) and both probes may be double stranded DNA molecules, the first probe (1) couples to the particle with at least two attachment points and the second probe (2) couples to the solid support with at least two attachment points. In addition the first and second probes have regions to bind a second molecule (9) different from the target analyte (3), in such a manner that when both target and second molecule bind to the probes the entire complex is made of two strands, one strand contains the target and the other the second molecule. If a rotational force is applied to the magnetic particle by rotating a magnetic field, torsional stress is accumulated in the complex, which forms supercoils that dramatically shorten the end-to-end distance of the complex after a certain level of torsional stress is reached. Therefore, supercoiling can be readily detected as a reduction in the displacement of the particle (4) under an applied force or as a reduction in the Brownian motion of the particle. This strategy can be used to increase the specificity and the discrimination of non-specific interactions in the system. The torsional stress in the complex tends to disrupt mismatched targets faster than perfectly matched ones. Therefore, requiring for target detection that a bead displace first, and then the complex supercoils, imposes a second condition that increases target specificity. In addition, non-specific interactions can be discriminated because non-specifically bound beads cannot supercoil.

In other embodiments, and referring to FIG. 5B, the first probe is a circular double stranded DNA molecule, wherein one of the strands has a discontinuity in a region designated as "active segment" (10). The circular molecule is not capable of supercoiling because of this discontinuity. The discontinued strand has flaps that have sequence complementary to different regions of the target analyte (3). When the target analyte binds (3) to the active segment (10), it bridges the two sides of the discontinued strand, which enables the circular molecule to supercoil. If a rotational force is applied to the first probe, for example by an intercalator molecule, torsional stress is accumulated in the probe, which forms supercoils that dramatically change the conformation of the probe. Therefore, supercoiling can be readily detected as a change in the displacement of the particle (4) under an applied force or a change in the Brownian motion of the particle (4). As in the previous embodiments, this strategy can be used to increase the specificity and the discrimination of non-specific interactions in the system. In other embodiments, and referring to FIG. 5C, the first probe comprises a circular double stranded DNA molecule wherein one of the strands has a discontinuity and the particle comprises a fluorescent molecule (11). The first probe may have multiple fluorescent labels. The discontinuous strand has flaps that have sequence complementary to different regions of the target analyte (3). When the target analyte binds (3) to the active segment (10), it bridges the two sides of the discontinuous strand, which enables the circular molecule to supercoil. If a rotational force is applied to the first probe, for example by an intercalator molecule, torsional stress is accumulated in the probe, which forms supercoils that dramatically change the conformation of the probe. Therefore, supercoiling can be readily detected as a change in the displacement of the particle under an applied force or a change in the length of the complex under an applied force. As in the previous embodiments, this strategy can be used to increase the specificity and the discrimination of non-specific interactions in the system.

In some embodiments of the present invention, the displacement of the particles is detected using an imaging system, wherein the imaging system generates an image of the particles and/or the probes-target complex that is detected by a sensing device. The image can be a regular image or a transformed representation of the object such as a shadow. The imaging system consists of four main components: illumination, specimen, image forming part, and a detector, which are sequentially positioned on the spatial path. An example of an imaging system is the optical microscope, and in this case the image forming part is the lens/lenses. Optical microscopes are well known by those of skill in the art. Optical microscopes can visualize unstained samples using image contrast of scattering, absorption or phase contrast, or stained samples with fluorescence or other scheme of light emission. The light source employed in a microscope can be coherence light source (such as laser) or incoherent source (such as LED or white light source). The lenses of a microscope can be a single lens, a series of lenses, or a compound lens which is usually called an objective. A macroscope is another example of imaging system. The main difference between a macroscope and microscope is the lens/objective they use. The microscope lens usually has magnification equal or larger than 1×, meaning the size of image is larger than the object. That results in a small field of view. The macroscope lens can have magnification smaller than 1×, which allows for visualization of a large area. A lens-free imaging system is another example of an imaging system. This type of system uses a digital optoelectronic sensor array, such as a charged coupled device (CCD) or a CMOS chip to directly sample the light transmitted through a specimen without the use of imaging lenses between the object and the sensor plane (Greenbaum, Nat. Methods 2012, 9, 9, 889-895; Gurkan, U. A., et al., Biotechnol. J. 2011, 6, 138-149). The lensless ultra wide-field cell monitoring array platform (LUCAS) (Ozcan, A. and Demirci, U. Lab Chip, 2008, 8, 98-106) is an example of this type of microscopes. The LUCAS platform is based on recording the "shadow images" of microscopic objects onto a sensor array plane. Microscopic objects are uniformly illuminated with an incoherent light source or a laser. The cell shadow pattern is digitally recorded using a CCD or CMOS sensor array. A coherent imaging system is another example of image system. This type of system uses the object to modulate the illumination laser beam and makes the modulated beam interfere with a reference laser beam or the same illumination beam, then the interferential information is recorded to reconstruct the information of the object. Digital holography (Javidi, Opt. Lett., 2000, 25, 9, 610-612) and in-line holography (Xu, PNAS, 2001, 98, 20, 11301-11305) are examples of this technique.

In some embodiments, the displacement of the magnetic particles is detected from the induced current in a solenoid.

As noted above, the present invention also is directed to a kit for detecting a target analyte in a sample, the kit comprising a) a particle; and b) a first probe capable of binding to the analyte, and to either a solid support or to the particle, the first probe optionally comprising an elongated region between about 0.15 and about 20 μm long; c) packaging material; and optionally d) instructions for use. In a particular embodiment, the kit may further comprise a second probe capable of binding to the analyte at a location different than the location that the first probe binds to the analyte, and which also is capable of binding to either a solid support or to the particle. The second probe may optionally contain an elongated region between about 0.15 and about 20 μm long. If the first probe is for coupling to a solid support, the second probe is for coupling to the particle, and if the first probe is for coupling to the particle, the second probe is for coupling to the solid support. The packaging material would be known to one of ordinary skill, and in certain embodiments would include conventional bottles, vials, boxes, etc. The optional instructions for use would preferably include conventional printed materials included within the packaging material.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Example 1

This example demonstrates a procedure to detect a target in a sample at low concentration using magnetic beads. The first probe is generated in the following manner: A plasmid (approximately 10 kilo base pairs) is linearized using a restriction enzyme that cuts it once. Two types of short DNA molecules capable of being ligated to the linearized plasmid are purchased (IDT): the first short DNA molecule is labeled with Digoxigenin and the second has single stranded region complementary to part of the target. The two short DNA molecules are ligated to the linearized plasmid. The second probe, a biotin labeled single stranded molecule, is purchased (IDT) with a sequence complementary to part of the target. Super-paramagnetic beads (Life Technologies) coated with Streptavidin are purchased. The first and second probes are mixed at high concentration (>0.01 µM) with the sample and incubated for few minutes. Magnetic beads are added to the solution and incubated few minutes. In order to wash unbound molecules, the solution is exposed to an external magnet that attracts the magnetic beads removing them from the solution. The solution is extracted from the container and discarded. The external magnet is taken away and the beads are suspended in buffer solution. Beads are then flowed into a capillary tube previously functionalized with anti-digoxigenin proteins (Roche) and let sediment and interact with the surface of the tube. In order to wash unbound beads, new buffer solution is flowed while a magnet is passed over the capillary. A large magnet is placed over the capillary to lift remnant unbound beads. The beads that remain attached to the bottom of the capillary are imaged using an image sensor array directly in contact with the bottom of the capillary tube. The solution in the tube is flowed in one direction to drag the beads and then the direction of the flow is reversed to drag the beads in the opposite direction. Successive images of the beads during this process show that some beads move about 3 micrometers in each direction while the rest of the beads bound to the surface do not move or move significantly less. Beads that move about 3 micrometers in each direction are bound to the glass surface via the complex of probes and target. The initial concentration of target molecules in the sample determines the number of these beads.

Example 2

This example follows the same procedure as the previous example, but instead of flowing solution in the capillary tube to distinguish the beads tethered by probes, the Brownian motion of the beads is detected. The beads attached via the probes to the solid support undergo Brownian motion and move within a circle of about 1 micrometer diameter. These beads can be discriminated from the beads non-specifically attached to the solid support which move significantly less.

Example 3

This example demonstrates detection of a 60 nucleotide (nt) synthetic DNA oligonucleotide target having the sequence of a section of Mycobacterium tuberculosis rRNA. The first probe was purchased from IDT and consisted of a 24 nt single stranded oligonucleotide having a sequence complementary to the 3' end of the target and a 5' biotin modification. The second probe was generated in the following manner: A plasmid (8.5 kbps) was linearized using the restriction enzyme BsmB I (New England Biolabs), which cut the plasmid twice generating a large fragment (approximately 8.4 kbps/2.8 micrometers) with different 4 nt overhangs at each end, and a small fragment which was separated and discarded by agarose gel purification (QIAquick Gel Extraction Kit, Qiagen). The linearized plasmid was ligated using T4 ligase to two double stranded DNA fragments generated by hybridizing synthetic oligonucleotides. The first fragment had one end with an overhang compatible to one of the overhangs of the plasmid and the other end had a 30 nt overhang complementary to the 5' end of the target. The second fragment had one end with an overhang compatible to the other overhang of the plasmid, and the other end of the fragment had a 5' digoxigenin modification. The first probe was mixed with a solution containing the target and the temperature was raised to 65° C. for 1 minute and then incubated at room temperature for 10 minutes. The buffer contained 800 mM NaCl. A blocker oligonucleotide complementary to the first probe was added and incubated for 5 minutes. The second probe was added and incubated for 10 minutes. Super-paramagnetic beads (Life Technologies) coated with Streptavidin were added and incubated for 30 minutes. The mixture was then flowed into a glass capillary tube (50 mm×2 mm×0.2 mm) previously functionalized with anti-digoxigenin proteins (Roche) and beads were let sediment for 5 minutes. A 100 mM NaCl buffer solution was flowed to wash unbound beads. The beads that remained attached to the bottom of the capillary were imaged first in the absence of flow (45 images) and then in the presence of flow (160 microliters/minute, 45 images). Alternatively, the beads were imaged first with flow in one direction (160 microliters/minute, 45 images), and then with flow in the opposite direction (160 microliters/minute, 45 images). The optical system used to image the beads was composed of a LED ring light, a telecentric lens and a camera. The LED ring light provided a dark field illumination. The telecentric lens, which is popularly employed in machine vision, exhibited the same magnification for objects at different distances. The lens had a large depth of field of around 500 micrometers. The magnification of the system was 1:1 which helped to achieve a large field of view of 6.14 mm by 4.6 mm. According to the optical resolution of the lens, the image size of each particle was about 4 micrometers, which was sufficient to investigate the displacement of the particles. The camera used in the system had a inch complementary metal oxide semiconductor (CMOS) chip, which had 4384 by 3288 pixels with pixel size of 1.4 micrometer.

Figure 6A:
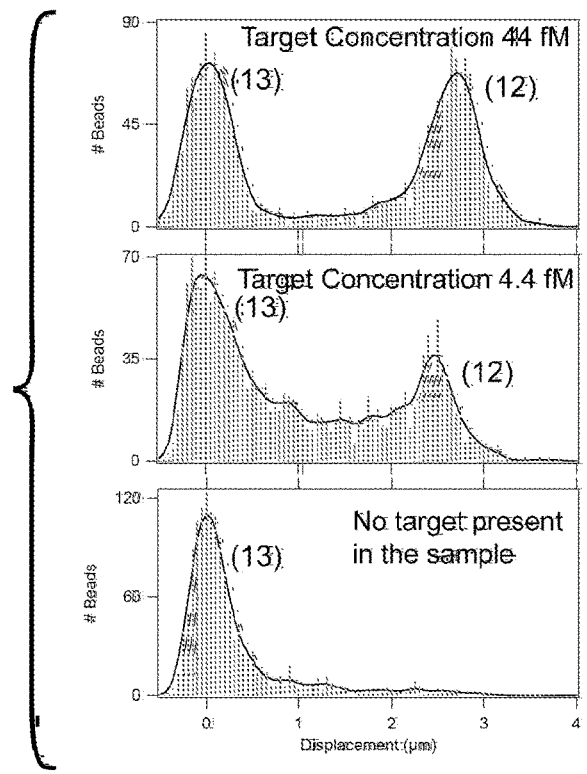
FIG. 6A shows histograms of bead displacement in experiments with 44 femtoMolar (fM) (top), 4.4 fM (middle) and no target (bottom). These histograms were generated using the embodiment of example 3. A first position for each bead was determined in images taken without flow and then a second position for each bead was determined in images taken with flow. Bead displacement is the distance between the first and second positions. In this embodiment, beads bound to a complex and coupled to the solid support via the second probe, which indicates target presence, are displaced by flow and form the peak on the right (12). Beads that are not displaced by flow form a peak on the left (13) and correspond to beads attached to the glass via a non-specific interaction.
Figure 6B:
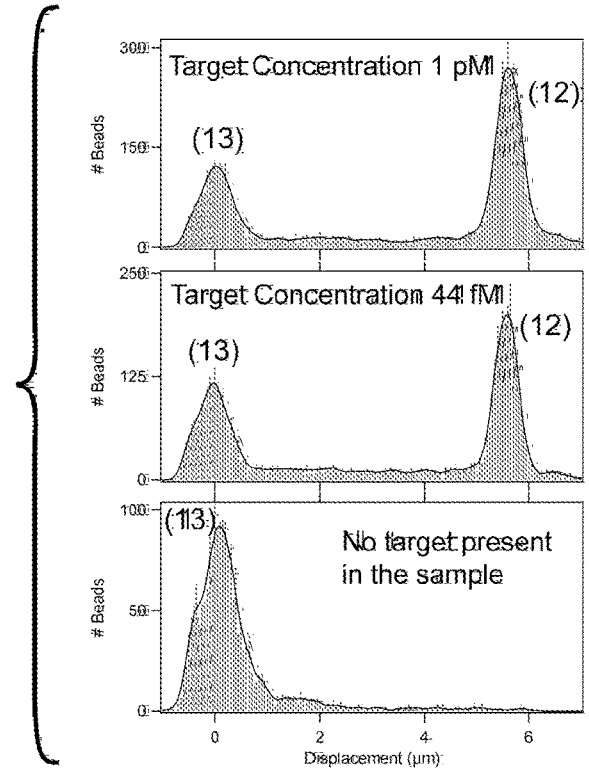
FIG. 6B shows histograms of bead displacement in experiments with 1 picoMolar (pM) (top), 44 fM (middle) and no target (bottom). These histograms were generated using the embodiment of example 3. A first position for each bead was determined in images taken with flow in one direction and then a second position for each bead was determined in images taken with flow in the opposite direction. Bead displacement is the distance between the first and second positions. In this embodiment, beads bound to a complex and coupled to the solid support via the second probe, which indicates target presence, are displaced by flow and form the peak on the right (12). Beads that are not displaced by flow form a peak on the left (13) and correspond to beads attached to the glass via a non-specific interaction.
Figure 7:
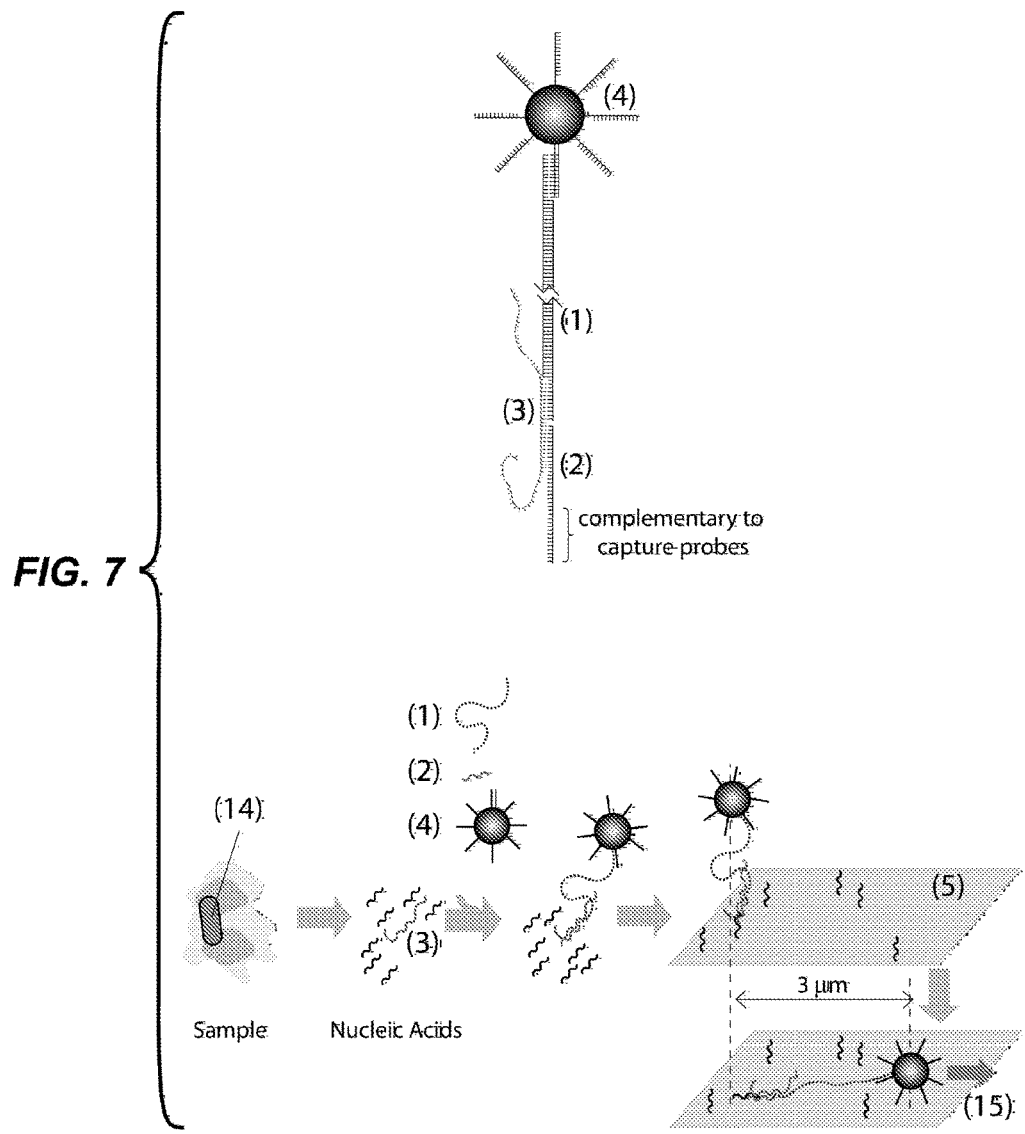
FIG. 7 depicts an embodiment for detection of bacterial cells, such as those causing tuberculosis in humans. In this example, the 23S ribosomal RNA (3) of the bacteria is detected using a first (1) and a second probe (2), each complementary to a different 30 nt sequence in the RNA molecule. The figures show particles functionalized with DNA oligonucleotides (4); a first probe (1) comprising an elongated region of about 9,000 DNA base pairs and 30 nucleotides overhangs at each end, one overhang complementary to the DNA oligonucleotides in the surface of the particles (4), the other overhang complementary to the target analyte (3); a second probe (2) comprising a DNA oligonucleotide, one part complementary to the target analyte (3) and another part complementary to capture probes for coupling to the glass substrate (5); and a glass substrate functionalized with capture probes (5). A sample, such as sputum or blood, containing the bacteria to be detected (14) is subjected to a process that lyses the cells, liberating their nucleic acids. The first probe (1), second probe (2) and particles (4) are exposed to the sample, so that a complex comprising the first and second probes and the target couples to a particle. The particle is flowed into a capillary tube where the second probe hybridizes to capture probes on the glass substrate. Images are taken in the absence and in the presence of fluid flow. Fluid flow generates a drag force (15) which displaces the particles that are tethered by a complex by about 3 µm.

A custom code written in Matlab was used to analyze the images and determine the displacement of most of the beads present in the field of view. Beads that were too close to each other (less than about 6 micrometers) were not included in the analysis. The position of a bead was defined as the average of its position in the 45 images. This system allowed measurement of the displacement of over 3,000 beads in each experiment with sub-micrometer resolution. The code generated a histogram of bead displacement (FIG. 6). When the first set of images was taken without flow (FIG. 6A), beads that moved more than 2.5 micrometers where considered bound to a target-probe complex (right peak in the histogram). Beads that moved less than 2.5 micrometers were considered non-specifically attached to the capillary surface. Most of beads that moved less than 2.5 micrometers moved less than 0.5 micrometers and had on average zero displacement. These beads usually numbered more than 2,000. When the first set of images was taken with flow (FIG. 6B), beads that moved more than about 5 micrometers where considered bound to a target-probe complex (right peak in the histogram).

What is claimed is:

1. A method of detecting a target analyte in a sample, the method comprising:
   a) providing a complex formed from:
      i) a first probe coupled to a particle and bound to said analyte if present, and
      ii) a second probe coupled to a solid support and bound to said analyte if present, so that if the target analyte is present in the sample, the particle is indirectly coupled to the solid support via a complex formed by the target analyte and the first and second probes, and wherein the complex comprises an elongated region; and
   b) either i) applying a force to the indirectly coupled particle or to the complex comprising the elongated region and measuring the amount of particle displacement or the length of the complex, wherein the amount of displacement or length of the complex indicates whether or not the target analyte is present in the sample, or ii) measuring the Brownian motion of the indirectly coupled particle, wherein the amount of Brownian motion indicates whether or not the target analyte is present in the sample.

2. The method of claim 1, wherein the first probe comprises a first antibody that binds to the target analyte and the second probe comprises a second antibody that binds to the target analyte.

3. The method of claim 1, wherein the first probe comprises a first nucleic acid that hybridizes to a first region of the target analyte and the second probe comprises a second nucleic acid that hybridizes to a second region of the target analyte.

4. The method of claim 3, wherein the target analyte is a nucleic acid, and the first and second probes bind to locations on the target that are at least about 500 nucleotides from each other.

5. The method of claim 1, wherein the elongated region is located on the first probe, the second probe, or the target analyte, or any combination thereof.

6. The method of claim 5, wherein the elongated region comprises a biomolecule or a non-biological polymer.

7. The method of claim 6, wherein the biomolecule comprises an elongated nucleic acid, polysaccharide, polypeptide, or combinations thereof.

8. The method of claim 5, wherein the elongated region comprises a polyethylene oxide (PEO), polyethylene glycol (PEG), poly(N-isopropylacrylamide) (PNIPAM), polyacrylamide (PAM), polyvinyl alcohol (PVA), polyethylenimine (PEI), polyacrylic acid, polymethacrylate or polyvinylpyrrolidone (PVP), or combinations thereof.

9. The method of claim 1, which further comprises the step of coupling the first probe to the particle.

10. The method of claim 1, which further comprises the step of coupling the second probe to the solid support.

11. The method of claim 1, which further comprises the steps of exposing the sample to the first probe and exposing the sample to the second probe.

12. The method of claim 11, wherein the further steps are performed in either order, or simultaneously.

13. The method of claim 12, further comprising a washing step after one or more of the steps.

14. The method of claim 13, wherein the first and second probes are exposed to the sample to form a solution; the particle is then added to the solution; the solution containing the particle is then added to a capillary to which the second probe binds to form a bound complex; the bound complex is washed; a first position of the particle is determined in the presence of an applied force or in the absence of an applied force; a second position of the particle is then determined in the presence of a force applied in a different direction or optionally in the absence of an applied force if the particle position was determined before in the presence of an applied force; and the particle displacement is determined from the first and second positions.

15. The method of claim 1, wherein the force applied to the particle is a magnetic force, a fluid buoyancy force, fluid drag force, mechanical force, electrical force, centrifugal force or a gravitational force.

16. The method of claim 1, wherein the force applied to the complex comprising the elongated region is generated with fluid flow, a receding meniscus, or a voltage gradient.

17. The method of claim 1, wherein the elongated region ranges from about 0.15 μm to about 20 μm in length.

18. The method of claim 1, wherein more than one target is detected in a single assay, and wherein the targets are differentiated based on different particle displacement or amount of particle Brownian motion they produce once the complex is bound to the solid support.

19. The method of claim 1, wherein at least one probe comprises an elongated region that has at least one internal loop that can be released or formed, and wherein releasing or forming the loop changes the amount of particle displacement.

20. The method of claim 19, wherein a change of force, or ionic strength, or temperature, or pH is used to release or form the internal loops of the probes.

21. The method of claim 19, wherein an auxiliary molecule is used to release or form the internal loops of the probes.

22. The method of claim 1, wherein more than one target is detected in a single assay, and wherein at least two different second probes are used which are coupled at different locations to the solid support before they bind to their targets, and wherein the targets are differentiated based on the location where the complex binds the solid support.

23. The method of claim 1, wherein the length or diameter of the particle ranges from about 0.3 μm to about 20 μm.

24. The method of claim 1, wherein the particle is a magnetic particle.

25. The method of claim 24, wherein the magnetic particle is superparamagnetic.

26. The method of claim 1, wherein the particle is fluorescent.

27. The method of claim 1, wherein the Brownian motion of the particle is measured in step b).

28. The method of claim 1, wherein the displacement of the particle is measured using an imaging system with a lens, or with a lens-free microscope, or with a coherent imaging technique.

29. The method of claim 1, wherein the target analyte is a nucleic acid molecule.

30. The method of claim 29, which further comprises controlling the temperature of the sample to produce denaturation of double stranded nucleic acids in the sample and/or specific hybridization of nucleic acids in the sample to the first and second probes.

31. The method of claim 29, wherein the sample is initially treated with an exonuclease enzyme to convert double stranded nucleic acids into single stranded nucleic acids.

32. The method of claim 1, wherein the target analyte comprises a protein, carbohydrate, lipid, hormone, steroid, toxin, vitamin, hapten, metabolite, drug or a combination thereof.

33. The method of claim 1, wherein the measurement of step b) is made with respect to multiple particles.

34. The method of claim 1, wherein the concentration of the target in the sample is estimated from the number of particles that have a particular displacement or Brownian motion.

35. The method of claim 1, wherein step b) comprises applying a twisting or rotational force to the indirectly coupled particle or to the complex, then measuring the amount of coiling in the complex.

36. A method of detecting a target analyte in a sample, the method comprising:
   a) providing a complex formed from:
      i) a first probe coupled to a particle and bound to said analyte if present, and
      ii) a second probe coupled to a substantially flat solid support and bound to said analyte if present,
   so that if the target analyte is present in the sample, the particle is indirectly coupled to the solid support via a complex formed by the target analyte and the first and second probes, and wherein the complex comprises an elongated region; and
   b) applying a force to the indirectly coupled particle using a force with a component parallel to the solid support that removes non-specifically bound particles, wherein the presence of the particle after the application of force indicates the presence of the target analyte in the sample.

* * * * *